US012748807B2

(12) United States Patent
Bouhnik et al.

(10) Patent No.: US 12,748,807 B2
(45) Date of Patent: Sep. 29, 2026

(54) MEDICAL PROCEDURE VIDEO SEARCHING USING MACHINE LEARNING

(71) Applicant: Intuitive Surgical Operations, Inc., Sunnyvale, CA (US)

(72) Inventors: Moshe Bouhnik, Holon (IL); Daniel Dobkin, Tel Aviv (IL); Emmanuelle Muhlethaler, Tel Aviv (IL); Roee Shibolet, Tel Aviv (IL)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 19/003,842

(22) Filed: Dec. 27, 2024

(65) Prior Publication Data

US 2025/0217413 A1 Jul. 3, 2025

Related U.S. Application Data

(60) Provisional application No. 63/616,247, filed on Dec. 29, 2023.

(51) Int. Cl.
*G06F 16/732* (2019.01)
*G06V 20/70* (2022.01)
*G16H 30/20* (2018.01)

(52) U.S. Cl.
CPC .......... *G06F 16/7328* (2019.01); *G06V 20/70* (2022.01); *G16H 30/20* (2018.01)

(58) Field of Classification Search
None
See application file for complete search history.

(56) References Cited

U.S. PATENT DOCUMENTS

2015/0153906 A1* 6/2015 Liao .................... G06F 16/7837 715/709
2020/0372295 A1* 11/2020 Jansen ................ G06F 18/2155
2021/0166807 A1* 6/2021 Quennesson ........... G06F 40/30
2022/0296334 A1* 9/2022 Fathollahi Ghezelghieh .............. G06N 3/09
2022/0351372 A1* 11/2022 Xin ........................ G06V 10/98
2022/0406469 A1* 12/2022 Nakagawa ............. G16H 50/50
2023/0153352 A1* 5/2023 Mondal ................ G06V 10/764 707/736

(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Richard L Bowen
(74) *Attorney, Agent, or Firm* — Foley & Lardner LLP

(57) ABSTRACT

Medical procedure video searching is described. A system can include a computing system. The computing system can include one or more processors, coupled with memory. The computing system can receive a search request including an image of a medical procedure and an indication of a type of the medical procedure. The computing system can generate, responsive to the search request, a search query based at least on the image with a model established for the type of the medical procedure. The computing system can identify, based at least on the search query, one or more videos of the type of the medical procedure from a collection of videos. The computing system can display, via a graphical user interface, the one or more videos of the type of the medical procedure.

20 Claims, 24 Drawing Sheets

(56) References Cited

U.S. PATENT DOCUMENTS

| | | | | |
|---|---|---|---|---|
| 2024/0331835 | A1* | 10/2024 | Peresie | G16H 40/67 |
| 2024/0339217 | A1* | 10/2024 | Bui | G16H 50/20 |
| 2024/0378230 | A1* | 11/2024 | Yu | G06F 16/583 |
| 2025/0062001 | A1* | 2/2025 | Subramanian | G16H 40/40 |
| 2025/0072979 | A1* | 3/2025 | Goldade | B25J 19/0066 |
| 2025/0209840 | A1* | 6/2025 | Ju | G06V 10/764 |

* cited by examiner

FROM FIG. 4A

TO FIG. 4C

Video: c20e1d01-fe53-4015-8295-
fa71b461cfef.mp4
Frame: 18935
k-NN Distance: 0.43

Video: 09f6cd76-29ea-4f01-812f-
523e1c06b2bc.mp4
Frame: 5577
k-NN Distance: 0.47

Video: 4b527535-2e2e-42ea-9889-

Video: 6a3aa1e5-8b6a-4149-a573-463ab23b4ea1.mp4
Frame: 15305
k-NN Distance: 0.43

Video: 02a4ff64-da73-4f45-9564-3dc1a91605cb.mp4
Frame: 9423
k-NN Distance: 0.47

Video: 145867f6-c59c-4d02-b788-

1105

Video: c20e1d01-fe53-4015-8295-fa71b461cfef
frame: 14835
path: /mnt/data/GIVideoFrame/S101/c20e1d01-fe53-4015-8295-fa71b461cfef/frame_014835.png
distance :0.198
crop :[0.2833333333333333, 0.2833333333333333, 0.7166666666666667, 0.7166666666666667]

Video: 02a4ff64-da73-4f45-9564-3dc1a91605cb
frame: 10223
path: /mnt/data/GIVideoFrame/S101/02a4ff64-da73-4f45-9564-3dc1a91605cb/frame_010223.png
distance :0.222
crop :[0.2833333333333333, 0.2833333333333333, 0.7166666666666667, 0.7166666666666667]

TO FIG. 11C

Video: a4bf1566-b590-4d7b-bc77-8a25cebd1fe8
frame: 10658
path: /mnt/data/GIVideoFrame/S101/a4bf1566-b590-4d7b-bc77-8a25cebd1fe8/frame_010658.png

FROM FIG. 11B

Video: c1f42c03-0d10-4364-811e-f9683c9460d4
frame: 14130
path: /mnt/data/GIVideoFrame/S101/c1f42c03-0d10-4364-811e-f9683c9460d4/frame_014130.png
distance :0.219
crop :[0.2833333333333333, 0.2833333333333333, 0.7166666666666667, 0.7166666666666667]

Video: 02a4ff64-da73-4f45-9564-3dc1a91605cb
frame: 14823
path: /mnt/data/GIVideoFrame/S101/02a4ff64-da73-4f45-9564-3dc1a91605cb/frame_014823.png
distance :0.225
crop :[0.2833333333333333, 0.2833333333333333, 0.7166666666666667, 0.7166666666666667]

Video: 4b527535-2e2e-42ea9889-4c5319cc51f1
frame: 7660
path: /mnt/data/GIVideoFrame/S101/4b527535-2e2e-42ea9889-4c5319cc51f1/frame_007660.png

TO FIG. 11D

FROM FIG. 11C

Video: c20e1d01-fe53-4015-8295-fa71b461cfef
frame: 18935
path: /mnt/data/GIVideoFrame/S101/c20e1d01-fe53-4015-8295-fa71b461cfef/frame_018935.png
distance :0.220
crop :[0.2833333333333333, 0.2833333333333333, 0.7166666666666667, 0.7166666666666667]

Video: f20579e1-ae65-43df-896c-161d0e88e457
frame: 15769
path: /mnt/data/GIVideoFrame/S101/f20579e1-ae65-43df-896c-161d0e88e457/frame_015769.png
distance :0.225
crop :[0.2833333333333333, 0.2833333333333333, 0.7166666666666667, 0.7166666666666667]

Video: 09f6cd76-29ea-4f01-812f-523e1c06b2bc
frame: 8077
path: /mnt/data/GIVideoFrame/S101/09f6cd76-29ea-4f01-812f-523e1c06b2bc/frame_008077.png

TO FIG. 11E

FROM FIG. 11D

Video: c1f42c03-0d10-4364-811e-f9683c9460d4
frame: 9730
path: /mnt/data/GIVideoFrame/S101/c1f42c03-0d10-4364-811e-f9683c9460d4/frame_009730.png
distance :0.221
crop :[0.2833333333333333, 0.2833333333333333, 0.7166666666666667, 0.7166666666666667]

Video: a44d5120-2d16-47ab-bea9-28363b3213a2
frame: 10015
path: /mnt/data/GIVideoFrame/S101/a44d5120-2d16-47ab-bea9-28363b3213a2/frame_010015.png
distance :0.228
crop :[0.2833333333333333, 0.2833333333333333, 0.7166666666666667, 0.7166666666666667]

Video: 393f2c7e-4373-4521-8b00-2a18dabd7bbf
frame: 14113
path: /mnt/data/GIVideoFrame/S102/393f2c7e-4373-4521-8b00-2a18dabd7bbf/frame_014113.png

TO FIG. 11F

Video: 491b0dfe-c635-46f7-b5d0-f7b664580192
frame: 13351
path: /mnt/data/GIVideoFrame/S101/491b0dfe-c635-46f7-b5d0-f7b664580192/frame_013351.png
distance :0.222
crop :[0.2833333333333333, 0.2833333333333333, 0.7166666666666667, 0.7166666666666667]

FROM FIG. 11E

Video: a44d5120-2d16-47ab-bea9-28363b3213a2
frame: 9515
path: /mnt/data/GIVideoFrame/S101/a44d5120-2d16-47ab-bea9-28363b3213a2/frame_009515.png
distance :0.228
crop :[0.2833333333333333, 0.2833333333333333, 0.7166666666666667, 0.7166666666666667]

Video: 50876601-d6b1-4993-b94d-993bc8598fe
frame: 16221
path: /mnt/data/GIVideoFrame/S101/50876601-d6b1-4993-b94d-993bc8598fe/frame_016221.png

MEDICAL PROCEDURE VIDEO SEARCHING USING MACHINE LEARNING

CROSS-REFERENCE TO RELATED PATENT APPLICATION

This application claims the benefit of priority under 35 U.S.C. § 119 to U.S. Provisional Patent Application No. 63/616,247, filed on Dec. 29, 2023, which is hereby incorporated by reference herein in its entirety for all purposes.

BACKGROUND

Videos of medical procedures can be recorded and stored in a data repository. However, due to the large number of videos that can be stored, and the lack of tags applied to the recorded videos, it can be technical challenging for a search engine to reliably and efficiently identify a particular video of a medical procedure responsive to a search query.

SUMMARY

Technical solutions disclosed herein can include search of medical procedure videos with machine learning. A system can utilize machine learning to perform a search of a collection of medical procedure videos with a query image or frame. Specifically, self-supervised learning can be used to perform the search, in some implementations. A medical practitioner can review one video and select a particular image or frame to act as a query image with which to query the collection of medical procedure videos. The system can implement feature extraction to identify semantic information of frames, clips, or videos. The system can implement an efficient training phase or pipeline, and a usage phase or pipeline. In the training pipeline, machine learning techniques, such as self-supervised learning techniques, can build a model which, given an input image, can produce a feature vector. The training can be done at a training site before deployment to a client premises, and the data used for training can be data that was acquired from various medical procedures. In some implementations, the training can be performed on-premises, or tuning can occur on the premise of the client (e.g., in the hospital) or on the cloud, and the data used for the training can be client data recorded by the client. The training pipeline can produce a collection or database of clustered video clips of medical procedures. For example, the system can utilize a model trained with self-supervised machine learning to produce an embedding that provides a representation of features of an image or video in a high dimensional space. The system can execute clustering with the embeddings of the medical procedure videos to generate distinct clusters of semantically similar videos or clips. For example, the system can execute clustering to cluster multiple videos of medical procedures into clusters of video clips from videos that include semantically similar frames. The system can select a keyframe or medoid for each cluster to run searching against. For a particular query image, the system can generate an embedding of the query image, and search the embedding against the embeddings of keyframes for each cluster. In the usage phase, the trained models can be available for immediate use to perform a search. For example, when a query image is provided by a user, the model process can process the query image to produce the feature vector. The feature vector can be searched in the vector database.

At least one aspect of the present disclosure is directed to a system. The system can include at least one computing system including one or more processors, coupled with memory. The system can include a first computing system to implement training of models and a second computing system to execute the models. The computing system can receive a search request including an image of a medical procedure and an indication of a type of the medical procedure. The computing system can generate, responsive to the search request, a search query based at least on the image with a model established for the type of the medical procedure. The computing system can identify, based at least on the search query, one or more videos of the type of the medical procedure from a collection of videos. The computing system can display, via a graphical user interface, the one or more videos of the type of the medical procedure.

The computing system can train the model with a training dataset and a self-supervision machine learning process, the training dataset including images without labels of medical information in the images.

The computing system can receive, from a user device, a label of medical information included in the image of the medical procedure. The computing system can save the label to the collection of videos responsive to a selection of the collection of videos with the search query.

The computing system can generate the graphical user interface to include a video of the medical procedure. The computing system can receive, via the graphical user interface, a selection of the image from the video of the medical procedure. The computing system can search, with an embedding, the collection of videos responsive to the selection of the image. The computing system can generate data to cause the graphical user interface to display frames of the collection of videos.

The computing system can generate embeddings of the collection of videos with a second model trained with self-supervised machine learning. The computing system can search, with an embedding, the embeddings of the collection of videos to select the collection of videos.

The computing system can select, with the indication of the type of the medical procedure, the model from models. At least two models of the models can be trained on images of different medical procedures. The computing system can generate an embedding of the image with the selected model.

The computing system can generate embeddings of the collection of videos with a second model trained with self-supervised machine learning. The computing system can cluster the embeddings into clusters. The computing system can search, with an embedding, the clusters to select a cluster of the clusters including embeddings of the collection of videos.

The computing system can generate embeddings of the collection of videos with a second model trained with machine learning. The computing system can cluster the embeddings into clusters with machine learning. The computing system can select key frames for the clusters with a medoid selection process, the key frames to provide medoids for the clusters. The computing system can search, with an embedding, embeddings of the key frames to select a cluster of the clusters.

The computing system can sort the collection of videos based on a level of similarity between the image and the collection of videos. The computing system can generate data to cause the graphical user interface to display the sorted collection of videos.

The computing system can receive, via the graphical user interface, a selection of a portion of the image, the portion of the image including a medical instrument or biological matter. The computing system can generate an embedding of the image with the selection of the portion of the image.

At least one aspect of the present disclosure is directed to a method. The method can include receiving, by a data processing system including one or more processors, coupled with memory, a search request including an image of a medical procedure and an indication of a type of the medical procedure. The method can include generating, by the data processing system, responsive to the search request, a search query based at least on the image with a model established for the type of the medical procedure. The method can include identifying, by the data processing system, based at least on the search query, one or more videos of the type of the medical procedure from a collection of videos. The method can include displaying, by the data processing system, via a graphical user interface, the one or more videos of the type of the medical procedure.

The method can include training, by the data processing system, the model with a training dataset and a self-supervision machine learning process, the training dataset including images without labels of medical information in the images.

The method can include receiving, by the data processing system, from a user device, a label of medical information included in the image of the medical procedure. The method can include saving, by the data processing system, the label to the collection of videos responsive to a selection of the collection of videos with the search query.

The method can include selecting, by the data processing system, with the indication of the type of the medical procedure, the model from models. At least two models of the models can be trained on images of different medical procedures. The method can include generating, by the data processing system, an embedding of the image with the selected model.

The method can include generating, by the data processing system, embeddings of the collection of videos with a second model trained with machine learning. The method can include clustering, by the data processing system, the embeddings into clusters with machine learning. The method can include selecting, by the data processing system, key frames for the clusters with a medoid selection process, the key frames to provide medoids for the clusters. The method can include searching, by the data processing system, with an embedding, embeddings of the key frames to select a cluster of the clusters.

The method can include receiving, by the data processing system, via the graphical user interface, a selection of a portion of the image, the portion of the image including a medical instrument or biological matter. The method can include generating, by the data processing system, an embedding of the image with the selection of the portion of the image.

At least one aspect of the present disclosure is directed to one or more storage media storing instructions thereon, that, when executed by one or more processors, cause the one or more processors to receive a search request including an image of a medical procedure and an indication of a type of the medical procedure. The instructions can cause the one or more processors to generate, responsive to the search request, a search query based at least on the image with a model established for the type of the medical procedure. The instructions can cause the one or more processors to identify, based at least on the search query, one or more videos of the type of the medical procedure from a collection of videos. The instructions can cause the one or more processors to display, via a graphical user interface, the one or more videos of the type of the medical procedure.

The instructions can cause the one or more processors to receive from a user device, a label of medical information included in the image of the medical procedure. The instructions can cause the one or more processors to save the label to the collection of videos responsive to a selection of the collection of videos with the search query.

The instructions can cause the one or more processors to select with the indication of the type of the medical procedure, the model from models. At least two models of the models can be trained on images of different medical procedures. The instructions can cause the one or more processors to generate an embedding of the image with the selected model.

The instructions can cause the one or more processors to receive via the graphical user interface, a selection of a portion of the image, the portion of the image including a medical instrument or biological matter. The instructions can cause the one or more processors to generate an embedding of the image with the selection of the portion of the image.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. The foregoing information and the following detailed description and drawings include illustrative examples and should not be considered as limiting.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIGS. 11A-F is an example graphical user interface for user selection of a specific region in a medical query image to focus a search of a collection of medical procedure videos on.

DETAILED DESCRIPTION

Figure 1:
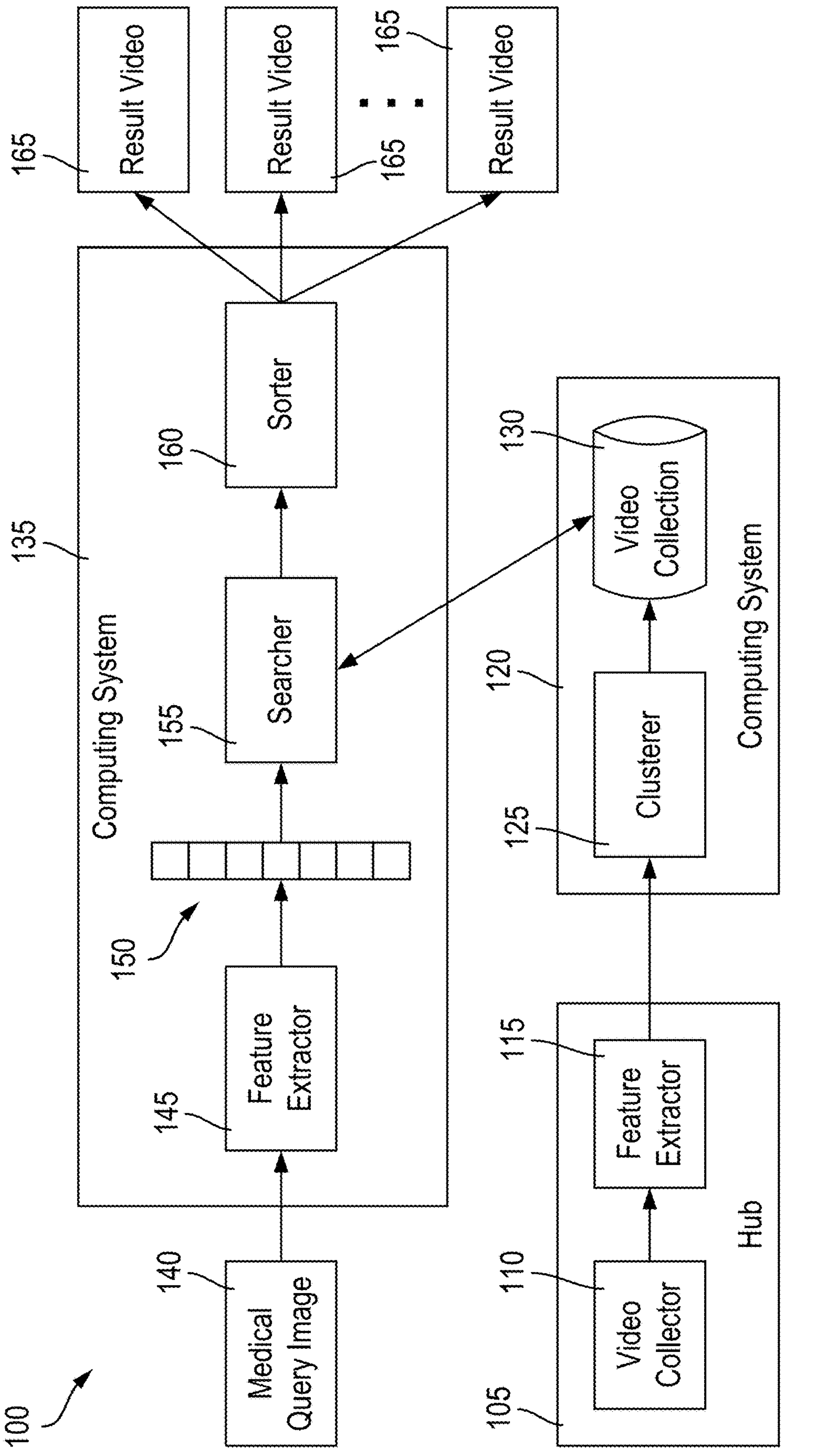
FIG. 1 depicts an example system to search medical videos.

Following below are more detailed descriptions of various concepts related to, and implementations of, methods, apparatuses, and systems to search videos of medical procedures. The various concepts introduced above and discussed in greater detail below may be implemented in any of numerous ways.

This disclosure is generally directed to an unsupervised image or clip search, and provides a framework that can support search of query images or video clips in a video collection. For example, a system can collect videos of medical procedures performed on patients with or without a medical robotic system by a medical practitioner, such as a surgeon, physician, doctor, nurse, or technician. A medical procedure can include, for example, irrigation, retroflection, biopsy, polypectomy, or any other invasive or non-invasive medical procedure. During the medical procedure, at least one camera or recording system can record a video of at least a portion of the medical procedure. The video of the procedure can be captured from within a cavity of the patient, via equipment such as an endoscope, or from an exterior of the patient. The system can collect video data of multiple medical procedures performed on one or multiple patients. The system can collect the video data for later review, presentation, case study, or educational purposes.

Because large amounts of various types of video data can be collected, it can be challenging to efficiently and reliably search for or identify a relevant video due to missing or inaccurate text-based annotations or metadata associated with videos, thereby causing erroneous search results, delays, latency, or excessive computing resource utilization.

To solve these, and other technical problems, technical solutions of this disclosure can include implementing searching of medical procedure videos with self-supervised machine learning. The self-supervised learning can provide a metric of semantic similarity, without using manual labels or truth data to implement training. A system can utilize self-supervised machine learning to enable a search of a collection of medical procedure videos with a query image or frame. A medical practitioner can review one video and select a particular image or frame to act as a query image with which to query the collection of medical procedure videos. The system can identify a selection of medical procedure videos or clips of medical procedure videos with a similarity to the query image, and return the medical procedure videos or the clips of the medical procedure videos for display to the medical practitioner.

The system can implement an efficient training pipeline for feature extraction to identify semantic information of frames, clips, or videos. The pipeline can produce a collection or database of clustered video clips of medical procedures. The collection can be updated once, periodically, or continuously. For example, the system can utilize a model trained with self-supervised machine learning to produce an embedding that provides a representation of features of an image or video in a high dimensional space. The system can execute clustering with the embeddings of the medical procedure videos to generate distinct clusters of semantically similar videos, clips, or frames. For example, the system can execute clustering to cluster multiple videos of medical procedures into clusters of video clips from videos that include semantically similar frames. The system can select a keyframe or medoid for each cluster to run searching against.

For a particular query image, the system can generate an embedding of the query image, and search the embedding against the embeddings of keyframes for each cluster. For a keyframe with an embedding that has at least a threshold level of similarity to the embedding of the query image, the system can retrieve and return at least a portion of videos or clips of the corresponding cluster. Because the search is run against the keyframes, and not every video or clip in the clusters, the system can return and display search results with low latency (e.g., in milliseconds, in seconds, in real-time, in near real-time). This can provide a user with a low latency search experience where clips or videos are rapidly or quickly displayed upon request (e.g., within milliseconds, within seconds, in real-time, in near real-time).

In some implementations, the system can produce models trained by self-supervised training procedures or processes for specific medical procedures. For example, the system can determine, based on metadata of a medical procedure video, what type of medical procedure the video is captured for. The system can aggregate multiple videos of different medical procedures, and train a model with each group of videos such that a model is created for each type of medical procedure. The system can utilize the model to generate embeddings for videos, images, or frames based on the procedure type of the videos, images, or frames. In this regard, because embedding models are produced for each medical procedure type, the search results provided by the system can be highly accurate.

Referring now to FIG. 1, among others, an example system 100 that performs medical video searching with self-supervised machine learning is shown. The system 100 can include one or multiple computing systems, e.g., computing systems to implement model training or computing systems to implement model execution. The computing systems can be separate or combined together. The computing system to implement model training and the computing system to implement model execution can have different system requirements. The computing systems can include graphic processing units (GPUs), general purpose processors, systems on a chip, etc. In some implementations, the training computing system can be implemented via at least one GPU. In some implementations, the computing system to implement model execution may not need to utilize a GPU, although a GPU can be used to provide faster model execution. The system 100 can include at least one hub 105. The hub 105 can be or include a data processing system, such as a computing system, a server system, a cloud system, or an on-premises system. The hub 105 can include or be connected with at least one camera, endoscope, or video database. The hub 105 can be coupled with systems, devices, or apparatus that record medical procedures performed on a patient (e.g., human or animal). The medical procedures can be invasive or non-invasive. For example, the medical procedures can include therapy, surgery, or diagnosis of diseases or conditions. The medical procedures can be in-patient or out-patient procedures. The medical procedures can include procedures performed from exterior of a patient (e.g., open heart surgery, skin grafting, or cesarean section delivery). The medical procedures can include procedures performed from within a cavity of the patient (e.g., irrigation, retroflection, biopsy, or polypectomy).

The hub 105 can include at least one video collector 110. The video collector 110 can be a piece of software, a software function, a software component, a script, a set of instructions, an executable, etc. The video collector 110 can collect and store medical procedure videos. For example, the video collector 110 can collect medical procedure videos from cameras, recording systems, storage systems, or databases. The video collector 110 can organize, segment, or store the medical procedure videos based on the type of medical procedure performed in each video. For example, the medical procedure videos can include data, metadata, tags, or labels that indicate the type of medical procedure that was performed in the video. For example, the types of medical procedures can be open heart surgery, skin grafting, cesarean section delivery, irrigation, retroflection, biopsy, or polypectomy. A medical practitioner can select or input an identification of the medical procedure into recording equipment before, after, or during a medical procedure.

The hub 105 can include at least one feature extractor 115. The feature extractor 115 can be a piece of software, a software function, a software component, a script, a set of instructions, an executable, etc. The feature extractor 115 can be or include a model trained by machine learning. The feature extractor 115 can extract features, semantic information, or a representation of an image, video, or video clip. The feature extractor 115 can generate an embedding or vector representing the image, video, or video clip. The feature extractor 115 can generate embeddings for a collection of medical procedure videos.

The hub 105 can store a set, group, or collection of feature extractors 115. Each feature extractor 115 can be trained to generate an embedding for images, videos, or video clips of a different medical procedure. A first feature extractor 115 can be trained to generate an embedding for medical procedure videos of a first type of medical procedure. A second feature extractor 115 can be trained to generate an embedding for medical procedure videos of a second type of medical procedure. The hub 105 can select a feature extractor 115 from the set of feature extractors 115 based on the procedure type of a medical procedure video that the hub 105 is to generate an embedding for. The hub 105 can receive a medical procedure video including metadata identifying a medical procedure type. The hub 105 can select one feature extractor 115 from the set of feature extractors 115 with the metadata. The hub 105 can match the medical procedure type indicated by the metadata against the medical procedures for the feature extractors 115 to select the one feature extractor 115 that generates embeddings for medical procedures of the medical procedure type. In some implementations, the hub 105 matches an identifier of a medical procedure against identifiers for the feature extractors 115 to select the one feature extractor 115 that generates the embedding for videos of the medical procedure type.

The feature extractor 115 can be a model trained based on self-supervised machine learning. The feature extractor 115 can be trained based on all or a portion of the collection of medical procedure videos collected by the video collector 110. The feature extractor 115 can be trained on-premises within a medical facility, such as a hospital, or on-premises within the medical facility. In some implementations, the feature extractor 115 can be trained on a computing system remote from the hub 105. The remote computing system can be a dedicated training system that delivers models to other systems, such as the hub 105. Once the feature extractor 115 is ready for execution or has been trained, the remote computing system can deliver the trained feature extractor 115 to the hub 105. In some implementations, the hub 105 can train the feature extractor 115. The hub 105 may train the feature extractor 115 on videos that the hub 105 captures, and not a full historical database of videos. In this regard, the feature extractor 115 can be tuned or fine-tuned by the hub 105 with videos that the hub 105 collects. A first feature extractor 115 can be trained for a first type of medical procedure based on only medical procedure videos of the first type of medical procedure. A second feature extractor 115 can be trained a second type of medical procedure based on only medical procedure videos of the second type of medical procedure. The hub 105 can implement self-supervised machine learning techniques, processes, or algorithms. The self-supervised machine learning technique can include joint embeddings, e.g., self-distillation with no labels (DINO) or masked Siamese network (MSN), auto encoders (AE), decoder-encoder models, masked auto-encoders (MAEs).

The feature extractor 115 can provide embeddings of the medical procedure videos to a computing system 120. The computing system 120 can be an on-premises system, an off-premises system, a computing system, a cloud platform, or a server system. The computing system 120 can include at least one clusterer 125. The clusterer 125 can be a piece of software, a software function, a software component, a script, a set of instructions, an executable, etc. The clusterer 125 can generate clusters of medical procedure videos. The clusterer 125 can generate clusters of medical procedure videos based on embeddings generated by the feature extractor 115.

The clusterer 125 can generate and store clusters of images, videos, or video clips in a video collection 130. The clusterer 125 can segment a video into multiple parts, segments, or clips based on the embeddings for the frames, images, or clips of the medical procedure videos. For example, the feature extractor 115 can generate an embedding for each frame or for groups of frames of the a medical procedure video. The clusterer 125, based on the embeddings of the frame so the medical procedure video or other medical procedure videos, generate a cluster of similar video clips. The clusterer 125 can implement at least one machine learning model, technique, process, or algorithm to cluster the medical procedure videos. For example, the clusterer 125 can segment medical procedure videos from a given database into semantically consistent parts, that include a descriptor that can be queried across videos. The clusterer 125 can generate video summarizations, e.g., keyframes, storyboards, static summaries, video skims. Furthermore, the clusterer 125 can perform temporal action segmentation, where an untrimmed procedural video is segmented temporally into multiple clips that represent different actions. The clusterer 125 can implement temporal action segmentation where there is a fixed transcript and a continuous or near continuous set of actions. Furthermore, the clusterer 125 can perform temporal action detection. The clusterer 125 can detect segments of action and inaction, and segment the medical procedure video into video clips of different actions of various lengths and with start and end times. The clusterer 125 can implement temporal action detection for medical procedure videos with a sparse set of actions. The clusterer 125 can implement temporally-weighted hierarchical clustering for unsupervised action segmentation (TWFINCH).

The resulting clusters can be video clips segmented or split from longer videos of medical procedures organized or grouped. Each video clip can be assigned at least one, or only one cluster. Each video clip can be labeled with a cluster identifier or value. The identifier or value can be random or pseudo-random. The identifier or value can be a counted value, e.g., one cluster can be labeled as a first cluster, another cluster can be labeled as a second cluster, etc. A user can review and provide a label for each cluster, e.g., if the user performs a search with a particular medical query image 140 and a particular cluster is selected, the user can provide a label or identifier for the video clips of the cluster, and the cluster can be labeled with the user provided label.

The computing system 120 can generate a set of clusters for each type of medical procedure. For example, the computing system 120 can generate a first set of clusters of videos or images of a first medical procedure by generating embeddings for the first set of videos or images with a first feature extractor 115, and then clustering the resulting embeddings to generate a first set of clusters. The computing system 120 can generate a second set of clusters of videos or images of a second medical procedure by generating embeddings for the second set of videos or images with a second feature extractor 115, and then clustering the resulting embeddings to generate a second set of clusters.

The computing system 120 can select keyframes. For example, the computing system 120 can select at least one keyframe for each cluster. The computing system 120 can select one keyframe per cluster. The computing system 120 can select multiple keyframes per cluster. For example, the computing system 120 can determine a number of keyframes to select for a cluster based on the size of the cluster. The computing system 120 can use a medoid selection process to select the keyframe for a cluster. Each keyframe can be a medoid for a cluster. For example, the computing system 120 can perform medoid selection by selecting a keyframe by identifying a frame that has a minimal dissimilarity to all other frames or video clips of the cluster. The keyframe can be a mean or centroid, in some implementations. The computing system 120 can generate a link or relationship between the keyframe for each cluster and the images, video clips, or videos of each frame. For example the keyframe can be marked or otherwise identified with a flag. Furthermore, an indication of the keyframe can be saved to each video, image, or video clip.

The computing system 120 can include at least one video collection 130. The video collection 130 can be a database, such as a vector database. The video collection 130 can be a structured query language (SQL) database, a not only SQL (noSQL) database, a Redis database, a library, or any other data repository or storage system. The computing system 120 can store a set, collection, or group of videos, images, or video clips. The computing system 120 store the embeddings of the videos, images, or video clips in the video collection 130. The computing system 120 can store the clusters of the videos, images, or video clips in the video collection 130.

The system 100 can include at least one computing system 135. The computing system 135 can be an on-premises system, an off-premises system, a data processing system, a cloud platform, or a server system. The computing system 135 can receive at least one medical query image 140. The medical query image 140 can be an image, frame, video, or video clip selected by a user via a user device, such as a laptop, tablet, console, smartphone, etc. The medical query image 140 can be selected by a user from a longer video of a medical procedure. For example, via a graphical user interface, a user can scan or seek through a video, and select one frame in the video for use as the medical query image 140.

The computing system 135 can generate at least one search query or embedding 150 with at least one feature extractor 145. The feature extractor 145 can be a piece of software, a software function, a software component, a script, a set of instructions, an executable, etc. The search query 150 can be a set of features, semantic information, or an embedding of the medical query image 140 with which to perform searching. The computing system 135 can store one or multiple feature extractors 145. For example, the computing system 135 can store one general feature extractor 145 that the computing system 135 applies to medical query images 140 of a variety of different medical procedures. The computing system 135 can store a feature extractor 145 different medical procedures, e.g., a first feature extractor 145 for a first type of medical procedure, a second feature extractor 145 for a second type of medical procedure. The feature extractors 145 can be trained or generated with videos or images of different medical procedures, e.g., generate the first feature extractor 145 for the first medical procedure type based on images or videos of the first medical procedure type, generate the second feature extractor 145 for the second medical procedure type based on images or videos of the second medical procedure type, etc.

The computing system 135 can implement machine learning training techniques to generate the feature extractor 145. For example, the computing system 135 can train the feature extractor 145 with a training dataset and a self-supervision machine learning process. The training technique can be self-supervised, and the training dataset can include images without labels of medical information in the images. For example, the images may not include labels or masks identifying objects of interest, medical instruments, polyps, cancer, tissue, organs, etc. The computing system 135 can implement self-supervised machine learning techniques, processes, or algorithms. The self-supervised machine learning technique can include joint embeddings, e.g., self-distillation with no labels (DINO) or masked Siamese network (MSN), auto encoders (AE), decoder-encoder models, or masked auto-encoders (MAEs).

The computing system 135 can receive an input query. The input query can include the medical query image 140 of a medical procedure and an indication of a type of the medical procedure. The medical query image 140 can include or be linked, related, or associated with an indication of a medical procedure. For example, a medical practitioner can provide an indication of the type of medical query image 140 is for. The computing system 135 can compare the indication of the type of the medical procedure of the medical query image 140 against indications of the medical procedures of the feature extractors 145. For example, the computing system 135 can compare the indication of the medical query image 140 against an indication of a first feature extractor 145 trained on images or videos of a first medical procedure type and compare the indication of the medical query image 140 against a second indication of a second feature extractor 145 trained on image or videos of a second medical procedure type. Based on the comparison, the computing system 135 can identify a match between an identifier of the medical procedure of the medical query image 140 and an identifier of the medical procedure a feature extractor 145. The computing system 135 can select, with the indication of the medical query image 140, a feature extractor 145. For example, the computing system 135 can select a feature extractor 145 that is trained based on images of the same type of medical procedure as the medical query image 140 is captured for.

The computing system 135 can generate an embedding 150 of the medical query image 140 with a model trained with machine learning for the type of the medical procedure of the medical query image 140. For example, the computing system 135 can generate an embedding 150 with the medical query image 140 and the feature extractor 145. For example, the computing system 135 can generate the embedding 150 with the medical query image 140 and the selected feature extractor 145. The computing system 135 can generate the embedding 150 by processing the medical query image 140 through the feature extractor 145.

The embedding 150 can be a representation of information in the medical query image 140. The embedding 150 can be a tensor, such as a vector. The embedding 150 can be a dense numerical representation of information in the medical query image 140 expressed as a vector. A space, such as a vector space, can quantify the semantic similarity between embeddings 150 or categories.

The computing system 135 can include at least one searcher 155. The searcher 155 can be a piece of software, a software function, a software component, a script, a set of instructions, an executable, etc. The searcher 155 can search the embedding 150 against the video collection 130. The searcher 155 can implement a matching or comparison technique to compare the embedding 150 against embeddings of the video collection 130. For example, the searcher 155 can search multiple embeddings of the video collection 130 with the embedding 150 to select one or multiple videos of the video collection 130. For example, the searcher 155 can search the clusters of the video collection 130 to select a cluster from the clusters. For example, the searcher 155 can compare the embedding 150 with embeddings of the clusters of the video collection 130. The searcher 155 can compare the embedding 150 against an embedding of a keyframe or medoid of each cluster. The searcher 155 can select a cluster from the video collection 130 based on the search responsive to an identification of a match level or similarity level greater than a threshold. The searcher 155 can select a cluster associated with a greatest match level or similarity level. For example, the searcher 155 can implement k-nearest neighbors to determine a similarity between the embedding 150 and the embeddings of the video collection 130. The searcher 155 can determine a distance measure between the embedding 150 and the embeddings of the video collection 130, e.g., Euclidean, cosine, sinusoid, etc.

The searcher 155 can implement searching based on various criteria. The criteria can be type of medical procedure, hospital site, surgeon identifier, medical procedure outcome, performance metrics, video annotation, texture, tool, or instrument. The user can provide the search criteria to the searcher 155 or the computing system 135. The searcher 155 can filter the result videos 165 with the various criteria. For example, each video collected by the video collector 110 can include an outcome indication, e.g., successful operation, unsuccessful operation, or requiring additional surgery. Each video can be linked, related, or tagged with the outcome of the medical procedure depicted in the video. If the user selects a particular outcome indication, such as successful, the searcher 155 can filter out any result video 165 that does not include the successful surgery tag. Furthermore, the searcher 155 can perform iterative searching. For example, the searcher 155 can perform iterative searching with the various criteria. For example, the user can recursively or iteratively filter or adjust the result videos 165 by changing or applying new or different search criteria or selecting or adjusting the medical query image 140 (e.g., cropping the image or making a selection within the image). The iterative searching can filter down a corpus of videos to smaller and smaller subsets of videos or clips with each addition of a new filtering criteria.

The video collection 130 can return the cluster of videos or segments of videos of the cluster based on the comparison of the embedding 150 with the embeddings of the video collections 130. The videos or video clips can be the result videos 165. The computing system 135 can include a sorter 160. The sorter 160 can be a piece of software, a software function, a software component, a script, a set of instructions, an executable, etc. The sorter 160 can determine a similarity or distance measure between an embedding of each result video 165 and the embedding 150. For example, the video collection 130 can provide a cluster of result videos 165 based on a comparison of the embedding 150 to an embedding of a keyframe or centroid of the cluster. The sorter 160 can utilize a feature extractor 145 to determine an embedding of images of each result video 165, and determine a similarity or distance measure between the embedding 150 and each result video 165 or segments or frames of each result video 165.

The sorter 160 can sort the result videos 165 based on a level of similarity between the medical query image 140 and the result videos 165. The sorter 160 can rank the result videos 165 in order of similarity between the embedding 150 and the embeddings of the video collection 130. The sorter 160 can cause the result videos 165 to be provided, displayed, or included within a graphical user interface displayed on a client or user device. For example, the computing system 135 can generate a graphical user interface to display the result videos 165 of medical procedures. For example, the computing system 135 can generate data that causes a user device to display the graphical user interface.

The computing system 135 can receive a label of medical information included in the medical query image 140 or in the result videos 165. For example, a user can provide a tag or label describing information in the medical query image 140 or in the result videos 165. For example, the user could provide an indication of an organ, a medical instrument, a polyp, bubbles, or other information. Responsive to receiving the label, the computing system 135 can apply the label to each of the result videos 165 or to segments of the result videos 165 returned by the searcher 155. The computing system 135 can save the label to the result videos 165 in the video collection 130.

Figure 2:
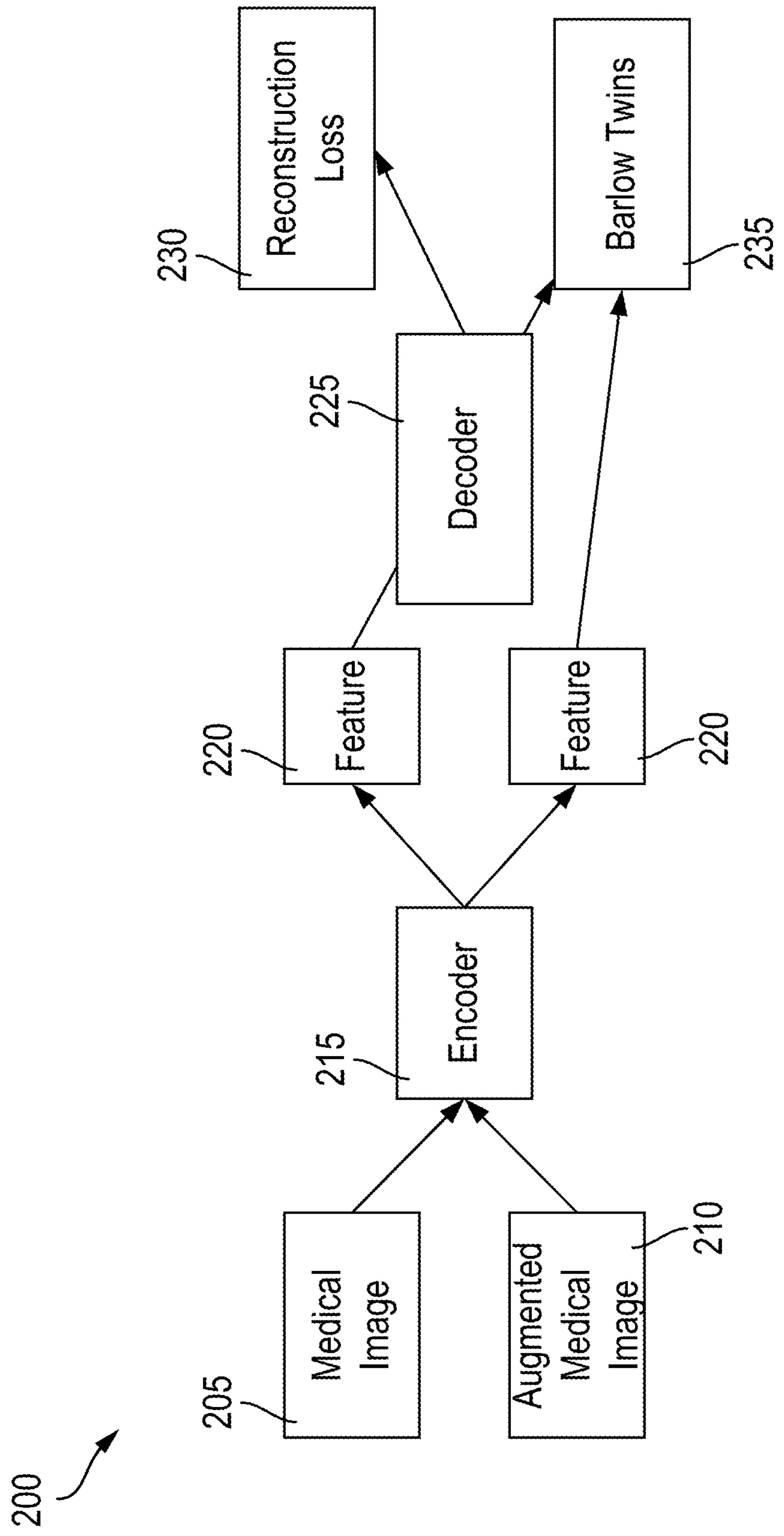
FIG. 2 is an example masked auto encoder for medical video searching with example reconstruction loss and Barlow twins loss.

Referring now to FIG. 2, among others, an example masked auto encoder 200 for medical video searching is shown. The masked auto encoder 200 can be trained with a medical image 205 and an augmented version of the medical image 210. The masked auto encoder 200 can be trained in a self-supervised manner by encoding and decoding the medical image 205, and encoding and decoding the augmented medical image 210 with an encoder 215 and a decoder 225. The auto encoder 200 can be trained to use the augmented medical image 210 to generate an internal state or compressed feature representation 220 that, when decoded, matches the medical image 205. A system can determine reconstruction loss 230 to measure how close the output of the decoder 225 matches the medical image 205 via a mean squared error (MSE) or another error measure. The masked auto encoder 200 can be trained through a Barlow Twins technique 235. The Barlow Twins technique 235 can be a self-supervised technique that measures a cross-correlation matrix between the embeddings of networks fed with distorted, augmented, or masked versions of the medical image 205. The masked auto encoder 200 can be trained with reconstruction loss, Barlow twins loss, additional losses, other augmentations, or different architectures.

Figure 3:
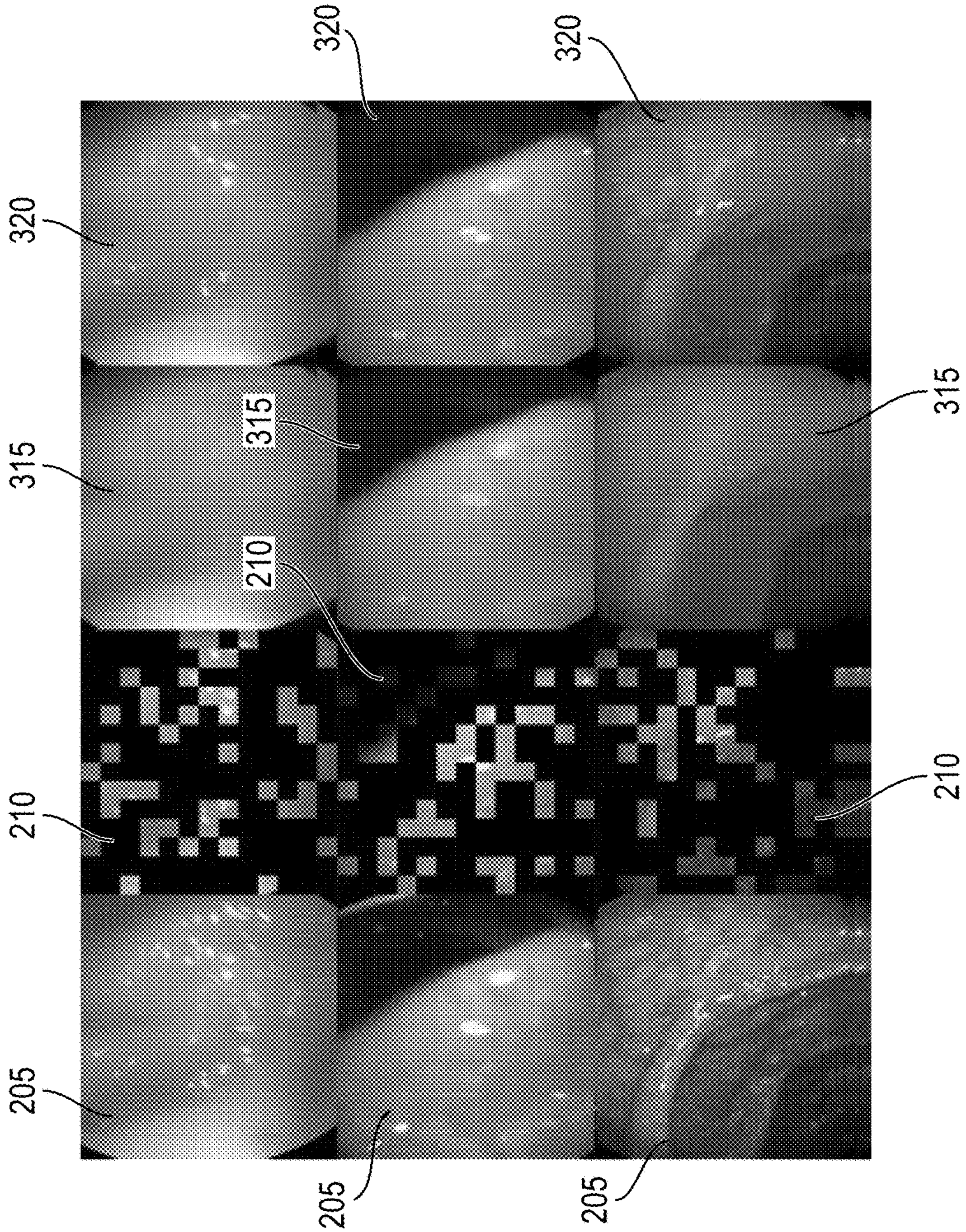
FIG. 3 is an example of augmented and masked training images.

Referring now to FIG. 3, among others, an example of augmented and masked training images is shown. The medical images 205 can be medical images of medical procedures. The medical images 205 can be original images that are not distorted, augmented, or masked. The images 210 can be masked versions of the medical images 205. The images 205 and 210 can be used to train a masked auto encoder 200. The images 315 can be decoded outputs of the network 200 from the images 205. The images 320 can be decoded outputs of the network 200 from the image 210.

Figure 4A:
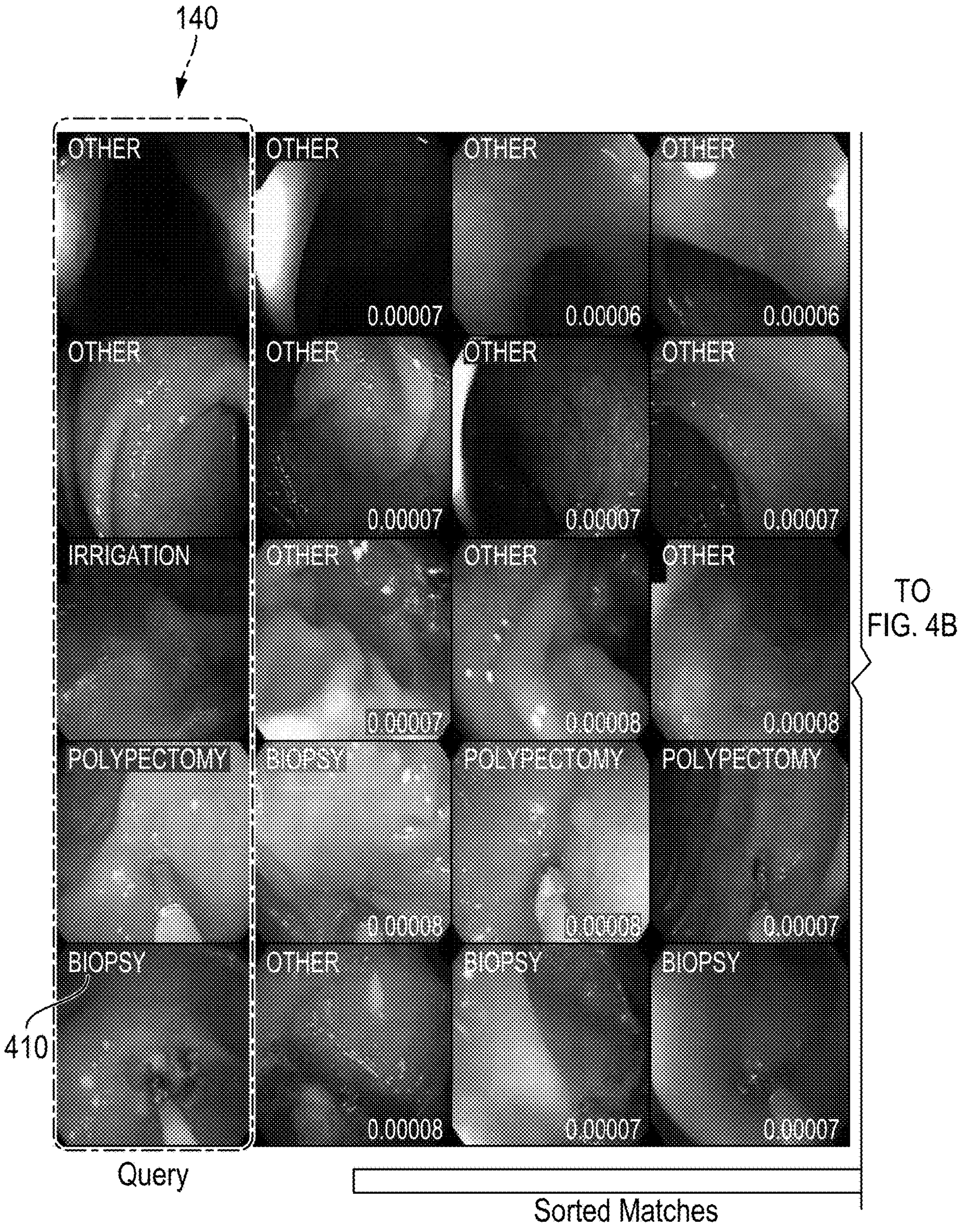
FIGS. 4A-C is an example of matches between medical query images and medical result images.
Figure 4B:
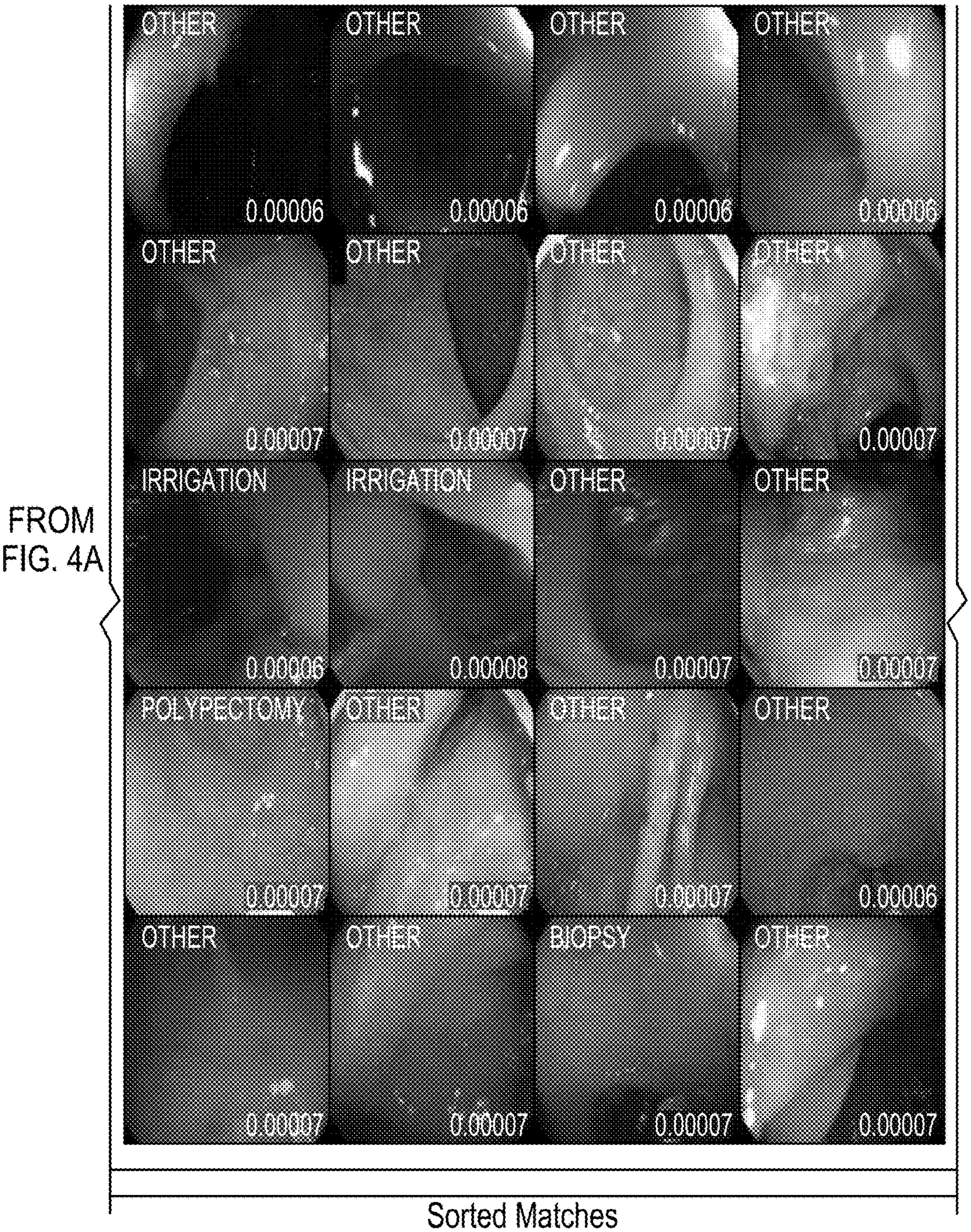
Figure 4C:
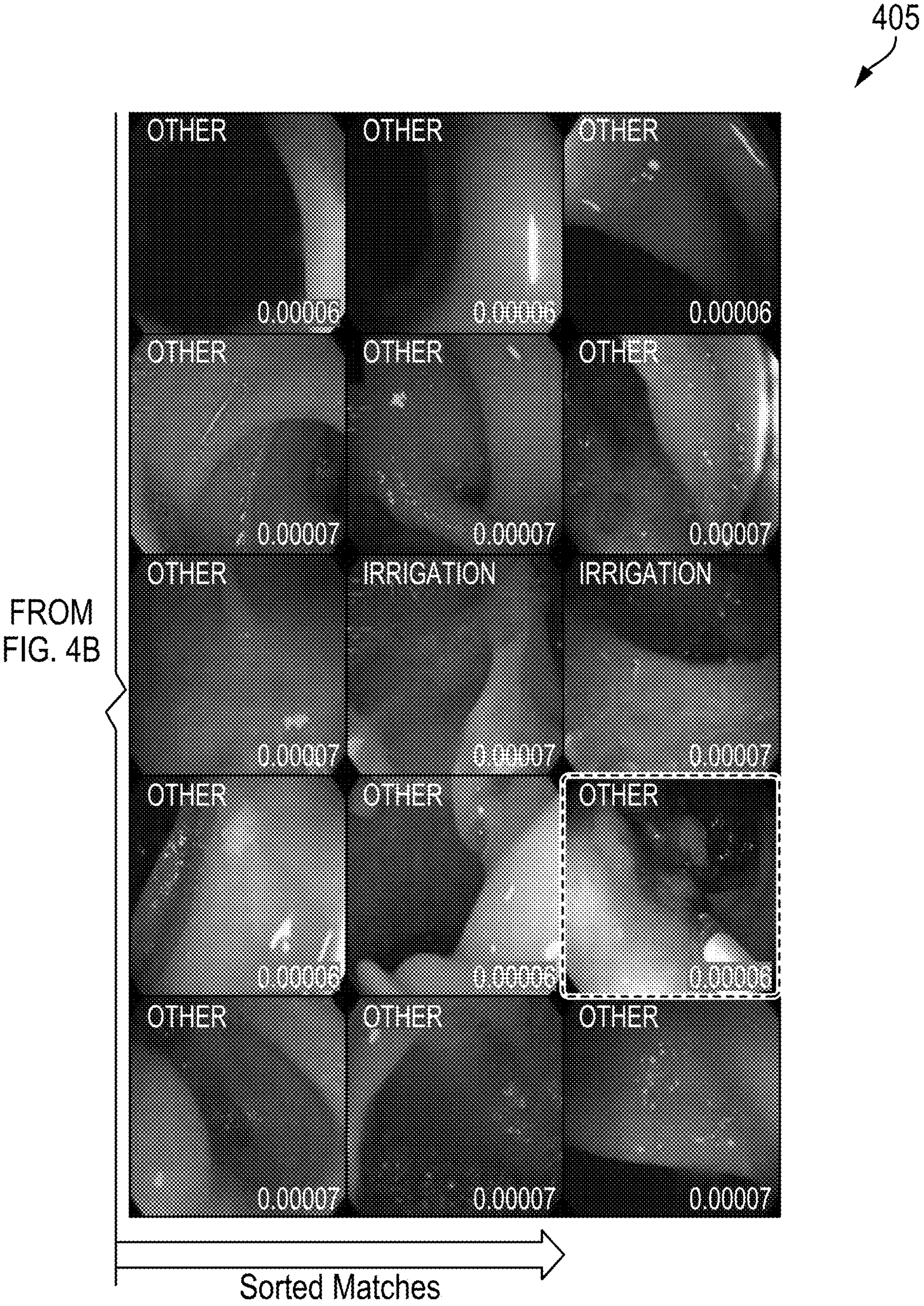

Referring now to FIGS. 4A-C, among others, example of matches between medical query images 140 and medical result images 405 are shown. For each medical query image 140, the searcher 155 can identify result images semantically similar to the medical query image 140. In FIGS. 4A-C, the result images 405 are displayed in a row corresponding to the medical query image 140. The sorter 160 can sort result images 405 based on a similarity or distance measure between the embedding 150 of the medical query image 140 and embeddings of each of the result images 405. The sorter 160 can rank the result images 405 to identify the top number of matches, e.g., a particular number of result images 405 that have the highest matches or matches with a similarity or k-match level greater than a threshold.

The medical query images 140 and the result images 405 can include labels 410. The labels 410 can indicate surgical objects, organs, procedures, biological matter, or other information of the medical query images 140 and the result images 405. The computing system 135 can compare the label 410 of the query image 140 against the labels of the result images 405 for that query image 140. The computing system 135 can detect whether the label of the query image 140 matches or does not match the labels 410 of the result images 405. Responsive to detecting a mismatch, the computing system 135 can correct the label of the mismatched result image 405. The computing system 135 can raise an alert to a user device and update the label 410 of the result image to the label 410 of the query image 140 responsive to receiving approval from a user. The computing system 135 can update the label 410 of the result image to the label 410 of the query image 140 without requiring user approval.

The images or frames of the videos of the video collection 130 can be labeled by a human or by a machine learning technique, such as a supervised machine learning technique. However, the human or supervised machine learning technique can mislabel or erroneously label the frames or videos of the video collection. Because the machine learning techniques implemented by the computing system 135, the hub 105, and the computing system 120 can be self-supervised, and may not rely on annotations or labels to implement the searching, the searcher 155 can identify or discover mislabeled videos or frames of the video collection 130. For example, a given label of the medical query image 140 can be compared against the labels for frames of the result videos 165, and if the labels do not match, the computing system 135 can identify an error in the frame or video labeling of the result videos 165. A user can provide input to correct or update the labels for the frames of the result videos 165. For example, for a set of frames retrieved based on a search with the medical query image 140, erroneous labels of the frames can be replaced with the label of the medical query image 140. The correction of the labels for the videos of the video collection 130 can improve the performance of systems that run against the videos of the video collection 130. For example, a supervised machine learning technique that can utilize the labels of the videos of the video collection 130 for training can be trained with increased accuracy due to the improvements in ground truth annotations in the video collection 130.

Figure 5:
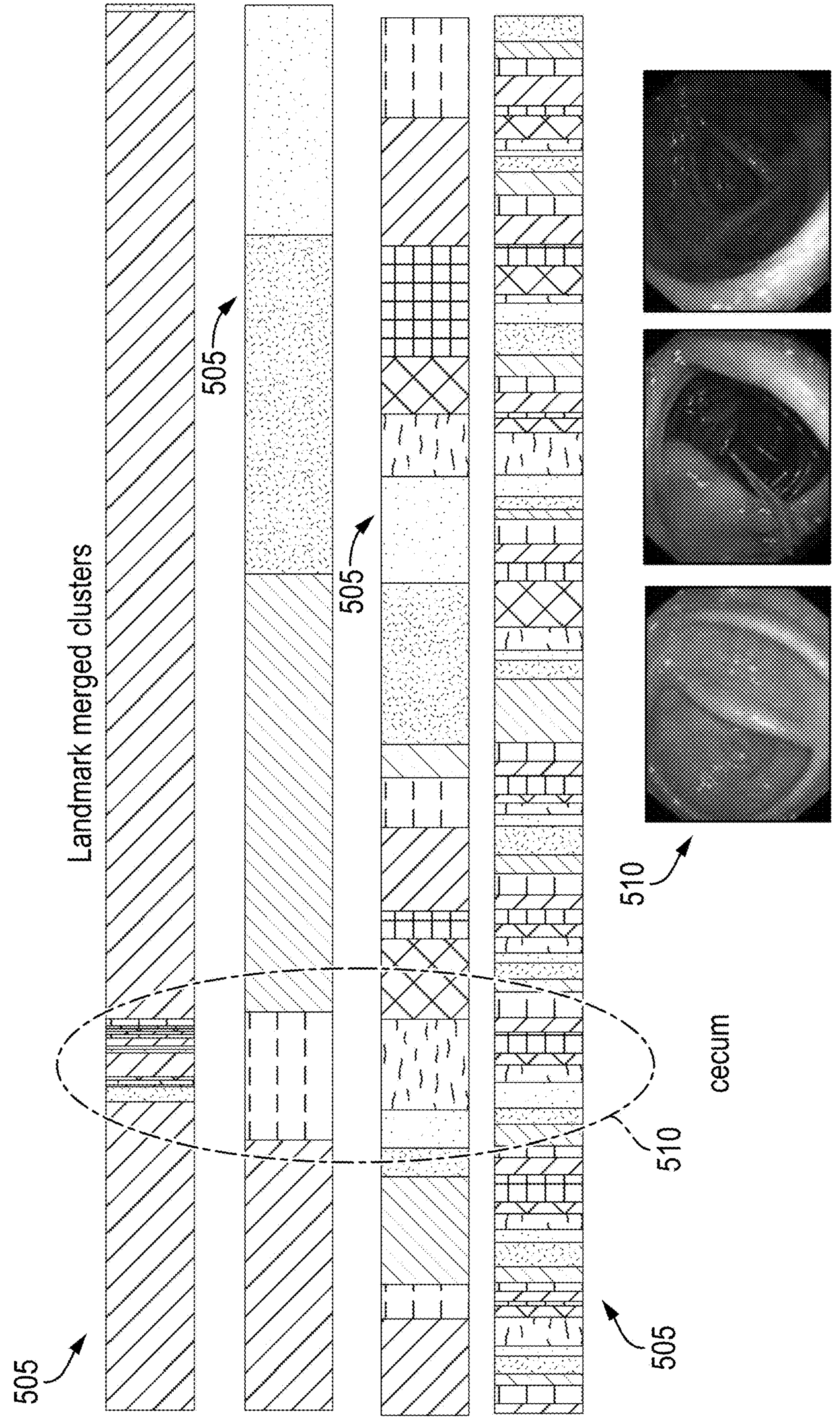
FIG. 5 is an example of landmark merged clusters of medical procedure videos of a cecum of a patient.
Figure 6:
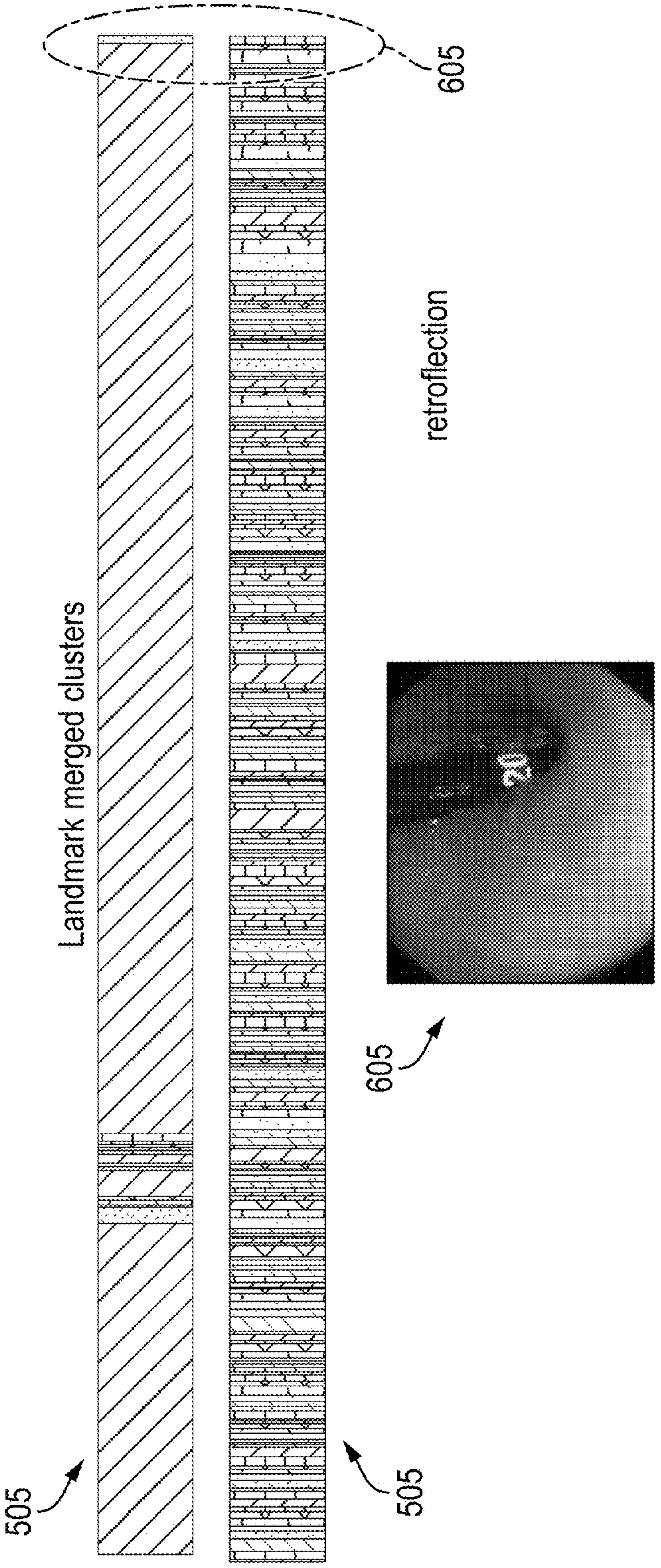
FIG. 6 is an example of landmark merged clusters of medical procedure videos of retroflection.
Figure 7:
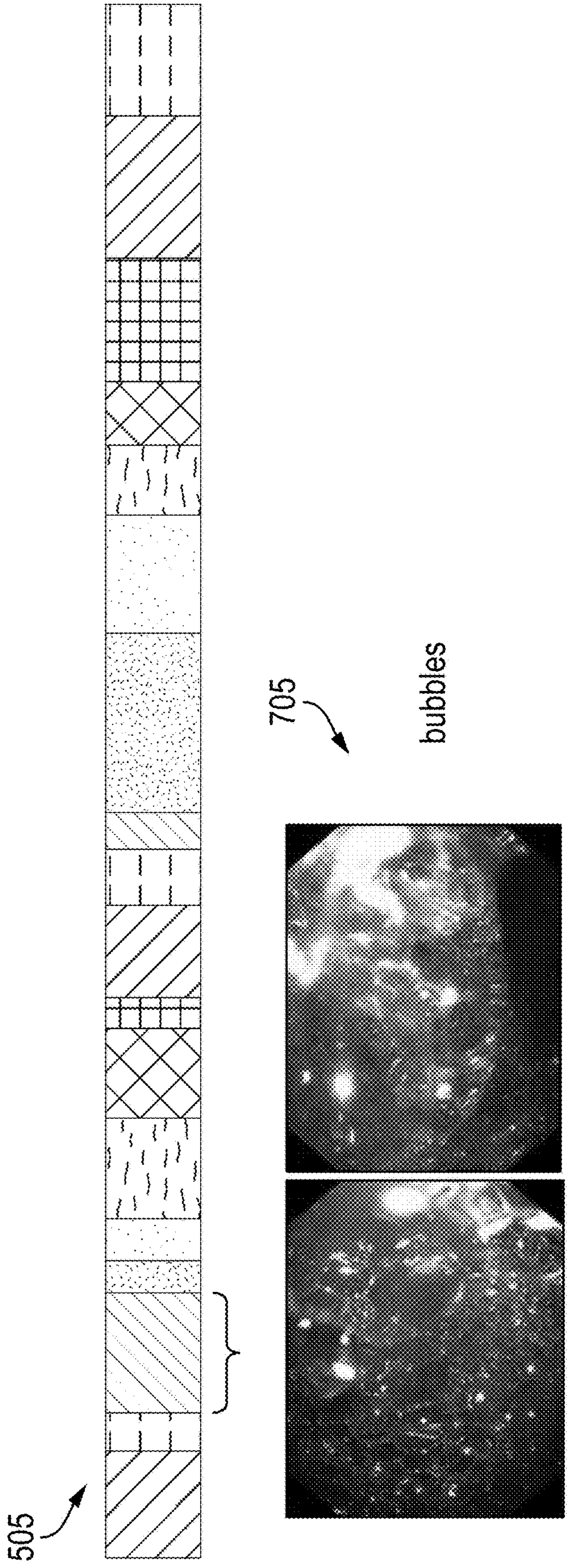
FIG. 7 is an example of clusters of medical procedure videos including bubbles.
Figure 8:
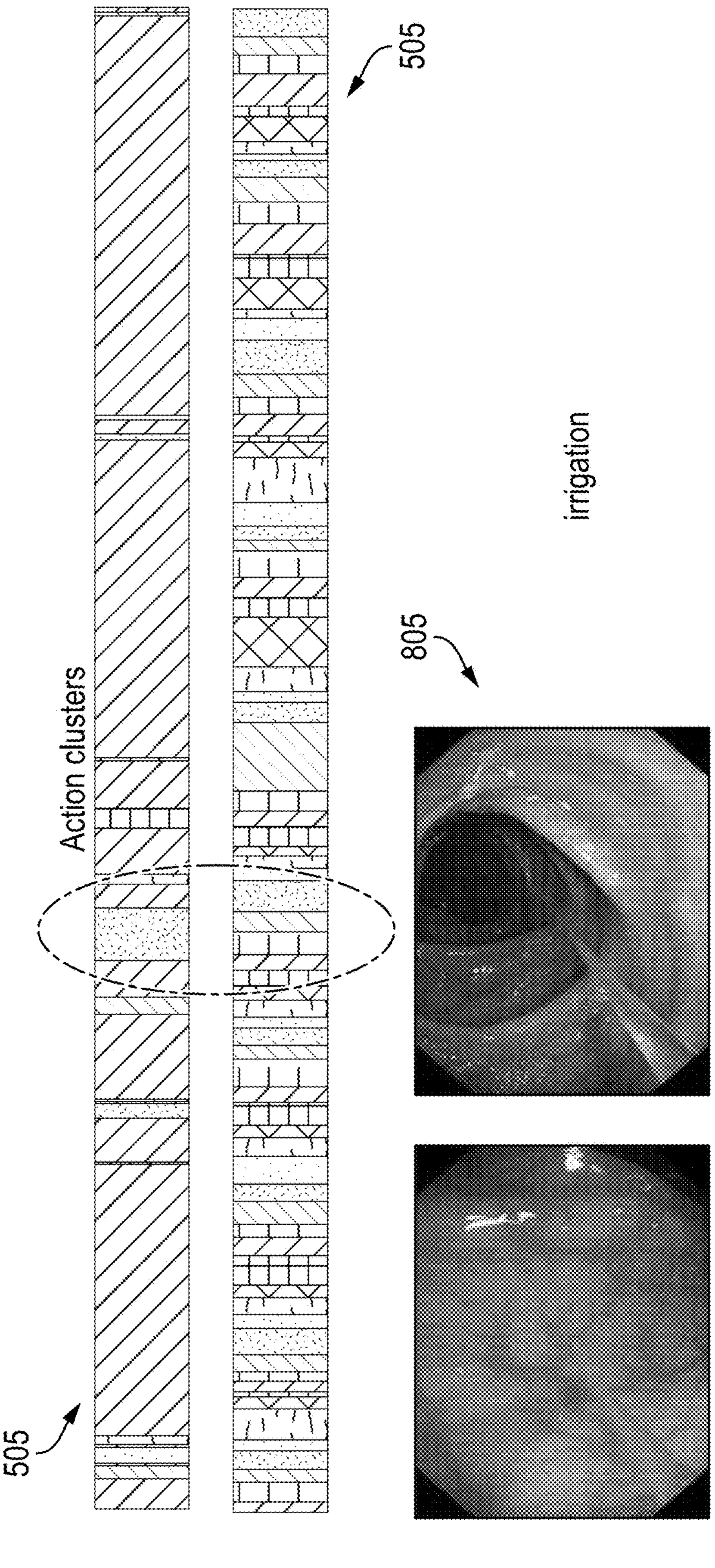
FIG. 8 is an example of action clusters of medical procedure videos of irrigation.

Referring now to FIGS. 5-8, example clusters of medical procedure videos 505 are shown. The medical procedure videos 505 can be videos collected by the video collector 110. The clusterer 125 can segment the videos 505 into multiple different segments based on landmarks. In FIGS. 5 and 6, the videos 505 are segmented based on landmark features. Landmark features can be organs, tissue, medical devices, surgical instruments, etc. For example, in FIG. 5, segments 510 of the videos 505 include a cecum of a patient, e.g., a pouch at the beginning of the large intestine, can be identified. For example, in FIG. 6, segments 605 of the videos 505 include a retroflection procedure performed during a colonoscopy. For example, in FIG. 7, segment 705 of the video 505 include bubbles. The clustering examples of FIGS. 5-8 can provide examples of an entire video, including multiple different phases, e.g., a view of a cecum or retroflection. Each patterned area can represent a different cluster within a video, for example, at 510 a cecum is present, at 605 retroflection is present, at 705 bubbles are present, etc. FIGS. 5-8 can provide a plot to illustrate correlation between clustering and events in the video. The computing system 135 can check that videos of retroflection are only one cluster, and similarly that videos with a cecum are only in one cluster or that bubbles are only in one cluster.

The videos 505 can further be clustered based on actions. For example, multiple videos 505 can be segmented and clustered. The videos 505 can be segmented and clustered based on actions. For example, in FIG. 8, the videos 505 can be segmented and clustered into segments 805 to indicate surgical irrigation. The videos 505 can be segmented and clustered to indicate polyp removal, incision, grafting, or any other medical procedure.

Figure 9:
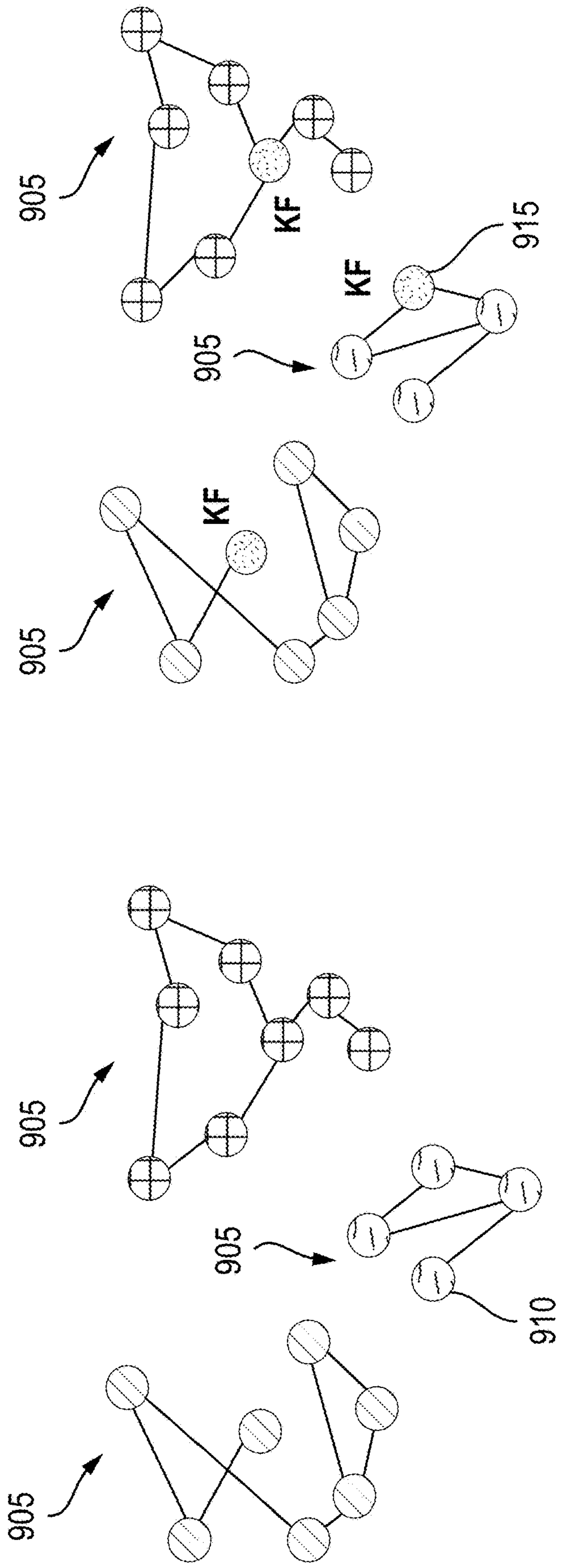
FIG. 9 is an example of clustered medical procedure videos and keyframes selected for clusters.
Figure 10A:
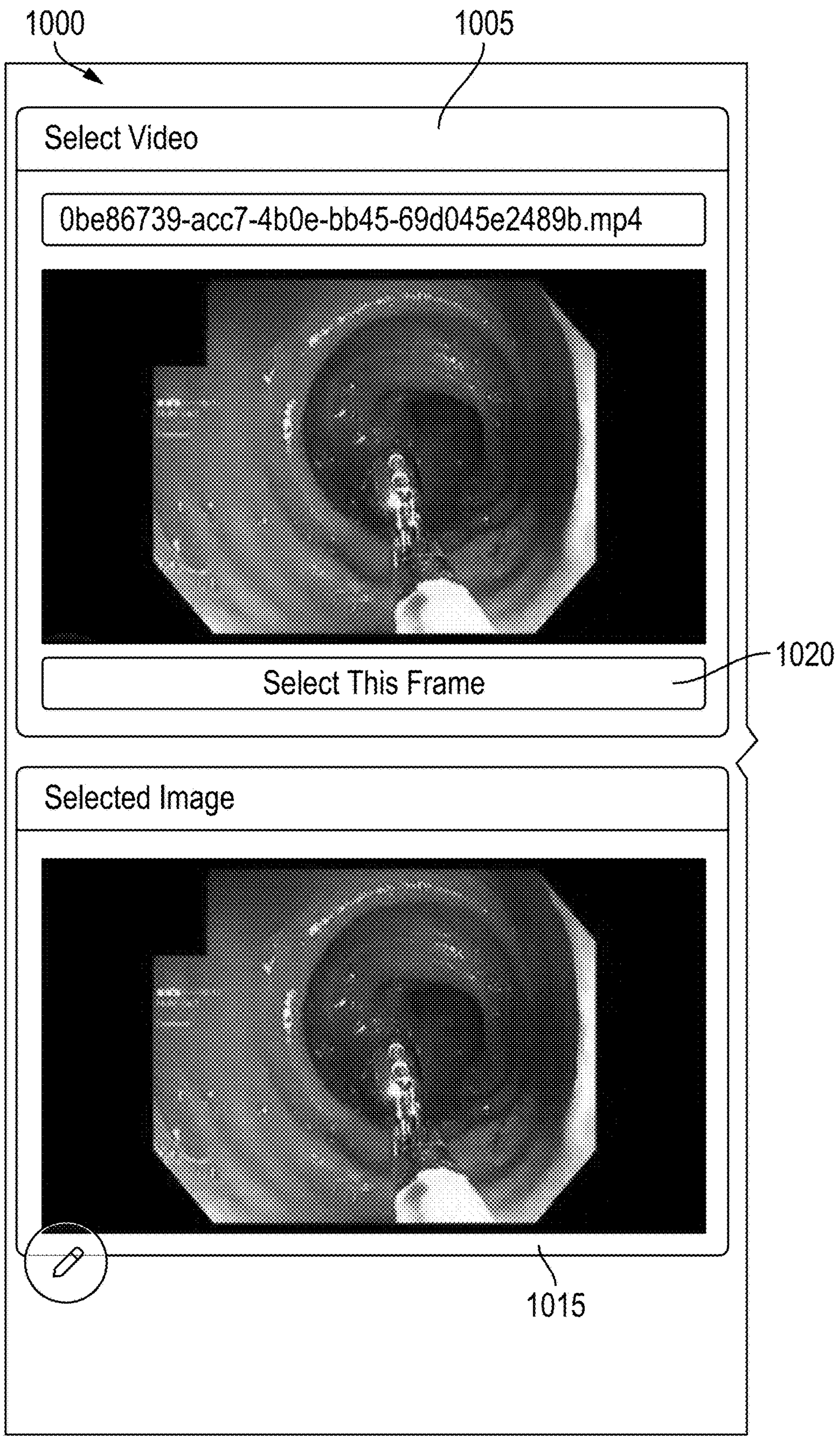
FIGS. 10A-D is an example graphical user interface to select a medical query image and to display medical result videos.
Figure 10B:
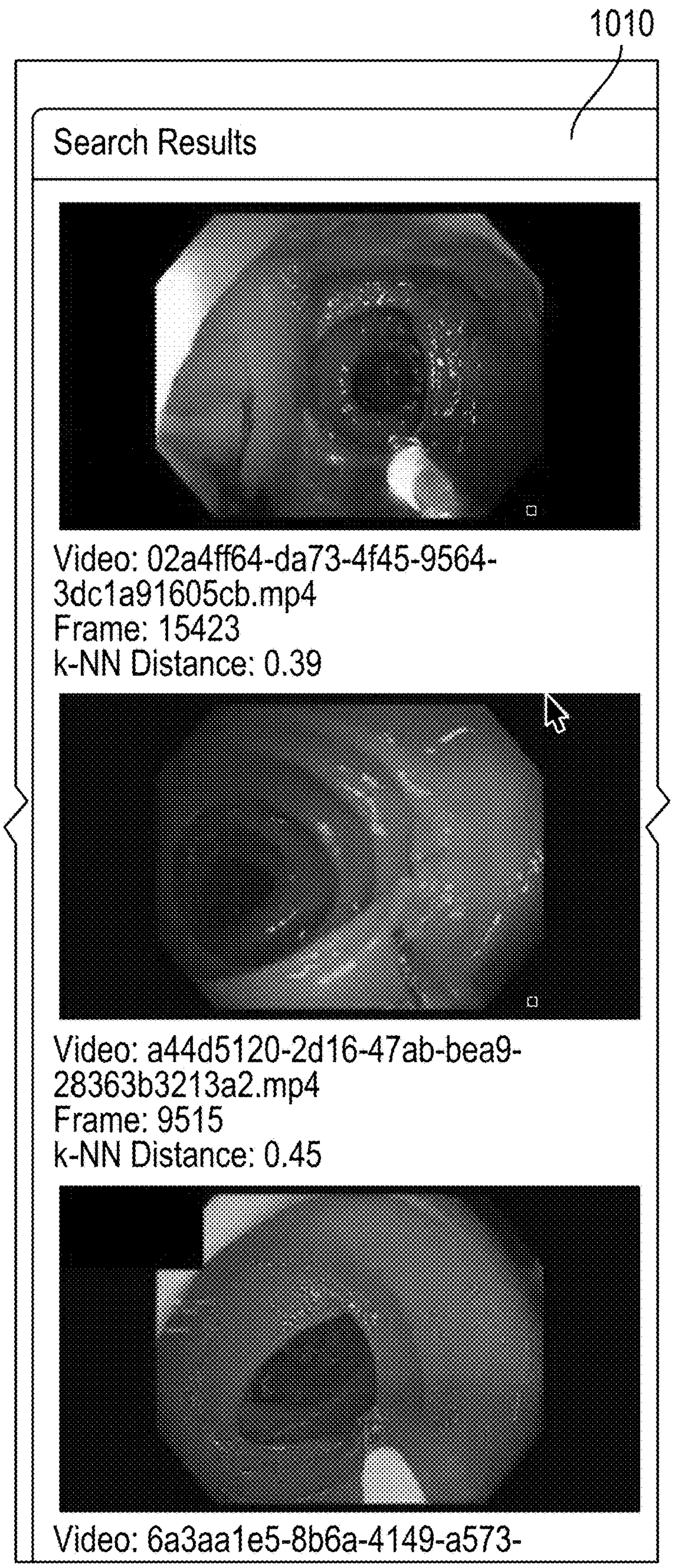
Figure 10C:
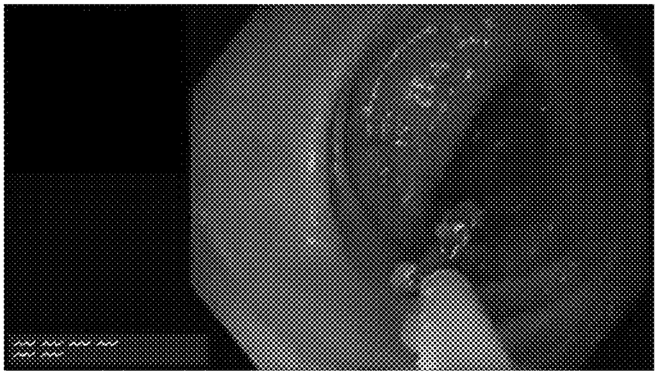
Figure 10C:
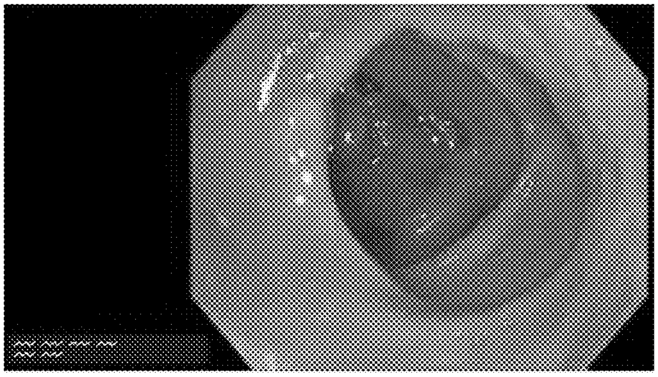
Figure 10C:
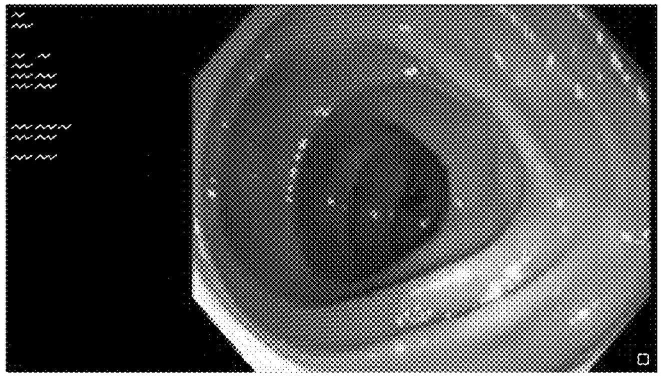
Figure 10D:
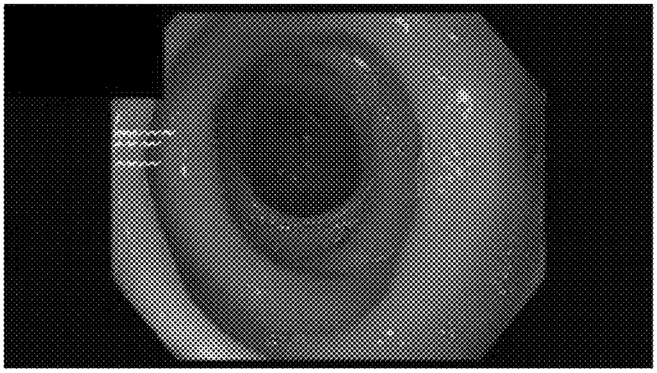
Figure 10D:
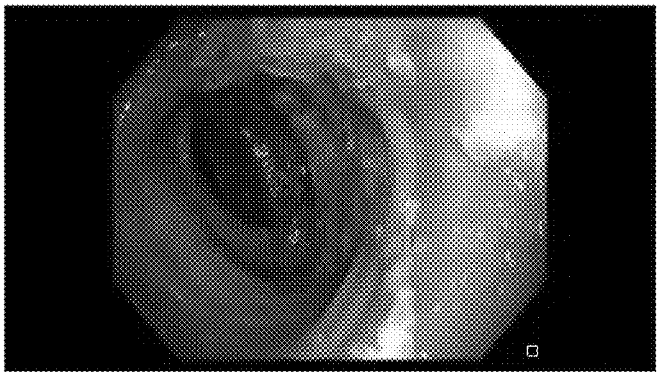
Figure 10D:
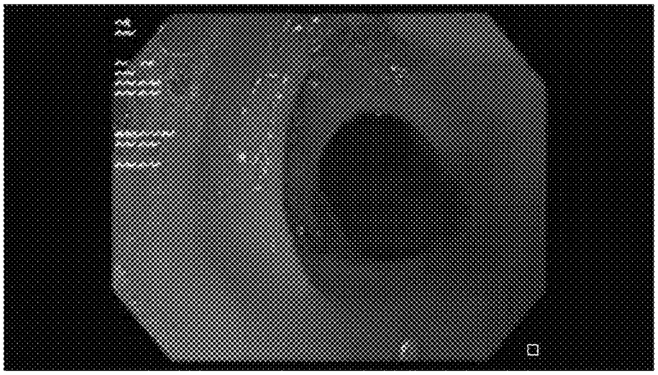
Figure 11A:
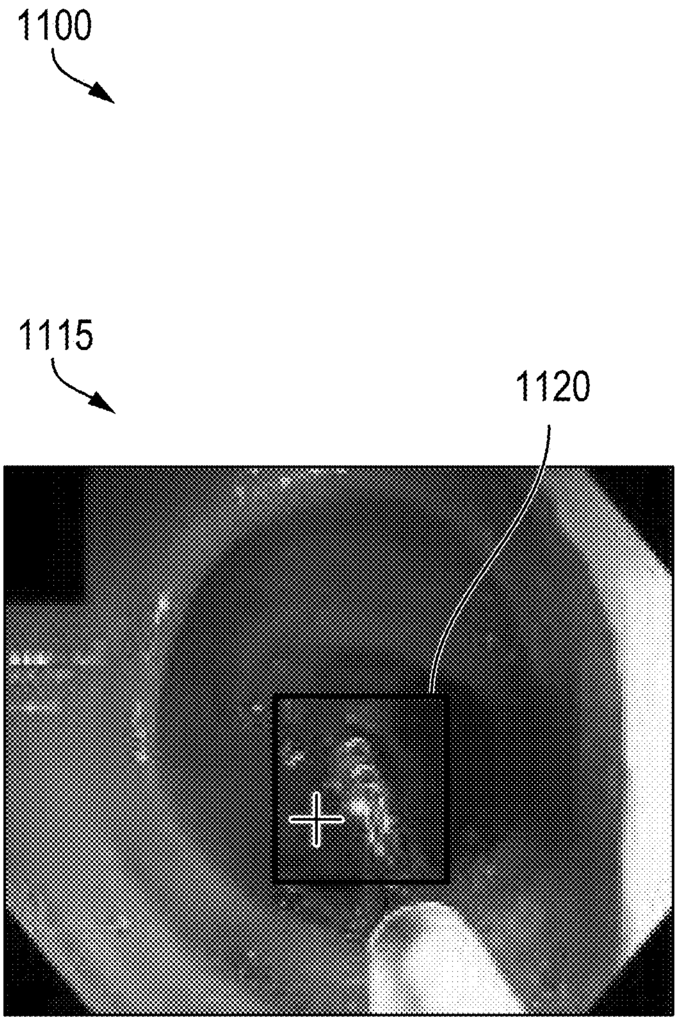
Figure 11B:
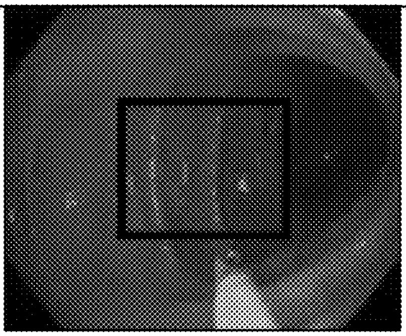
Figure 11B:
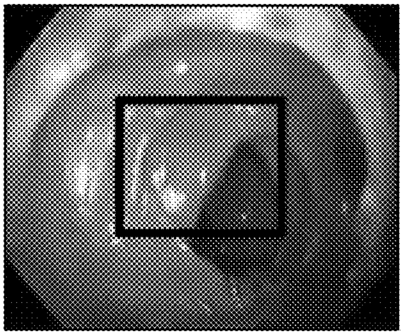
Figure 11B:
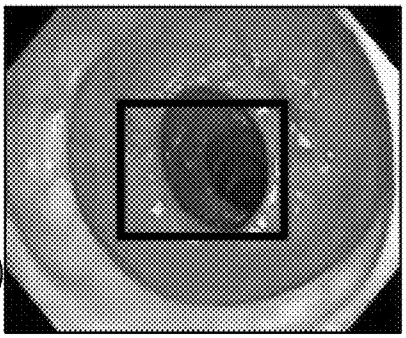
Figure 11C:
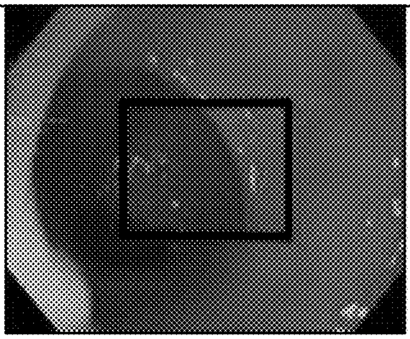
Figure 11C:
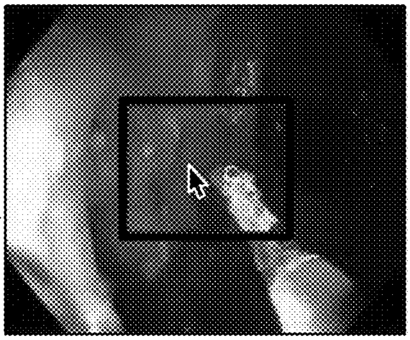
Figure 11C:
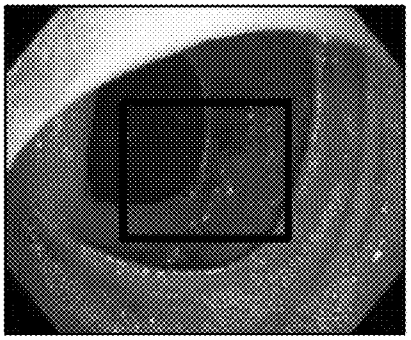
Figure 11D:
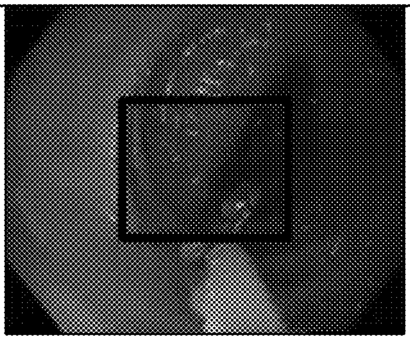
Figure 11D:
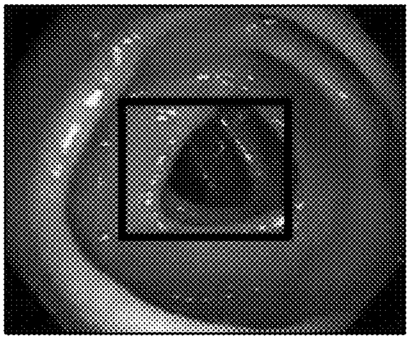
Figure 11D:
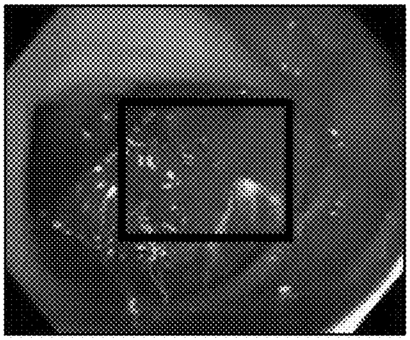
Figure 11E:
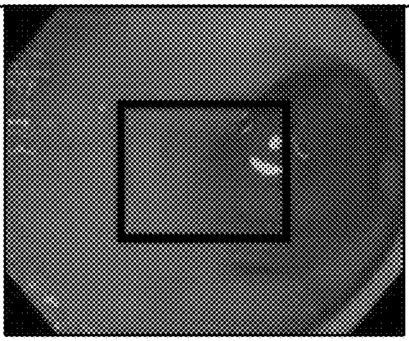
Figure 11E:
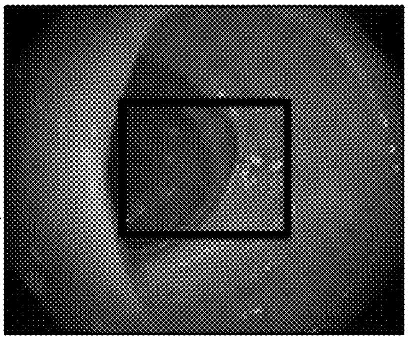
Figure 11E:
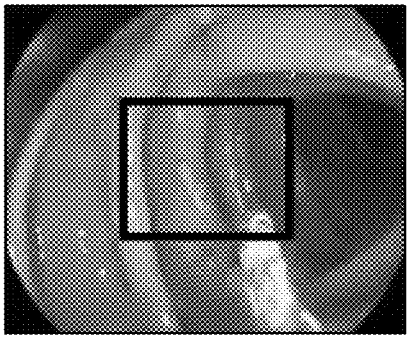
Figure 11F:
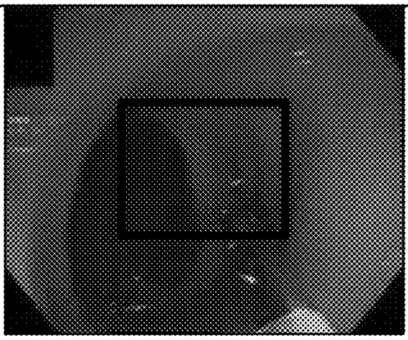
Figure 11F:
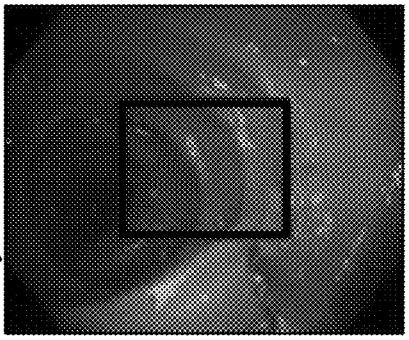
Figure 11F:
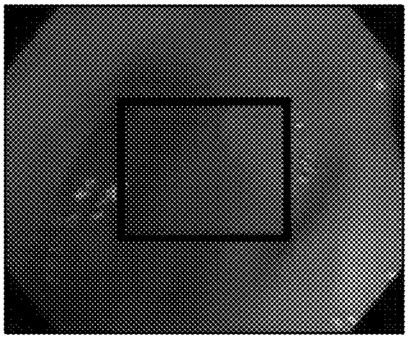

Referring now to FIG. 9, among others, an example of clustered medical procedure videos and keyframes selected for clusters is shown. The clusterer 125 can cluster segments, videos, or frames 910 into clusters 905. The clusterer 125 can implement clustering techniques such as temporally-weighted hierarchical clustering for unsupervised action segmentation (TWFINCH). For example, the feature extractor 115 can extract features for frames, segments, or videos of medical procedures. The feature extractor 115 can generate embeddings for videos of the video collection 130. The clusterer 125 can cluster the embeddings into different clusters 905 with a machine learning technique, such as TWFINCH.

The clusterer 125 can generate a cluster 905 to represent each action in video. The clusters 905 can be represented as graphs that indicate a first nearest neighbor frame, therefore taking into account time progression. The clusterer 125 can select a keyframe 915 for each cluster 905. The clusterer 125 can select a single keyframe 915 for each cluster 905. The clusterer 125 can select a number of keyframes 915 for a cluster 905 proportionally to the number of total frames 910 in the cluster 905. The clusterer 125 can select the keyframe 915 to provide a representative frame for the cluster 905. The clusterer 125 can select the keyframe 915 based on a level of similarity or a level of dissimilarity between each frame 910 relative to each other frame. The clusterer 125 can select the keyframe 915 to be a median level similarity, or median level dissimilarity. The clusterer 125 can select the keyframe 915 based on medoid selection, where a keyframe 915 is selected by identifying a frame 910 with a minimum level of dissimilarity to each other frame 910 in a particular cluster 905 and setting the keyframe 915 to be the identified frame 910.

Referring now to FIGS. 10A-D, among others, a graphical user interface 1000 to select a medical query image and to display medical result videos is shown. The computing system 135 can generate the graphical user interface 1000 to be displayed on a user device, such as a laptop computer, desktop computer, smartphone, tablet, or console. The computing system 135 can generate the graphical user interface 1000 to include a video of the medical procedure. The graphical user interface 1000 can include an element 1005. The element 1005 can display the video of a medical procedure. The video displayed in the element 1005 can be a video selected by a user via user input. The element 1005 can include a name or file name of the video. The computing system 135 can receive, via the graphical user interface 1000, a selection of an image from the video of the medical procedure. For example, the element 1005 can display a video and include a seek element to allow a user to scan or move between frames of the video. A user can seek, track, or move to a particular frame of the video, and interact with an element 1020 to select the frame to be the medical query image 140 to be used to search the video collection 130. Responsive to interacting with the element 1020, the selected image can be displayed in element 1015.

Responsive to receiving the selection, the feature extractor 145 can generate the embedding 150 from the medical query image 140, and the searcher 155 can search the video collection 130 with the embedding 150. The computing system 135 can generate data to cause the graphical user interface 1000 display the result videos 165. The computing system 135 can generate data to cause the graphical user interface 1000 to display the frames of the result videos 165. The graphical user interface 1000 can include an element 1010. The element 1010 can include the result videos 165. The result videos 165 can be loaded into the graphical user interface 1000 to play within the element 1010. The result videos 165 can be started or initiated at a frame identified by the searcher 155. The result videos 165 can include parts or segments that belong to different clusters. For example, the result videos 165 can be segmented into multiple parts, and the segments or frames of each result video 165 can belong to various clusters. The videos 165 can be retrieved based on a match between the embedding 150 and a particular cluster. The result videos 165 can be initialized at a frame that corresponds to the cluster identified by the searcher 155. The result videos 165 can be initialized at a frame with a closest or highest match to the medical query image 140. For example, for a given result video 165, the searcher 155 can identify a frame with a highest or closest match to the medical query image 140. For example, the searcher 155 can identify a lowest distance (or distance less than a threshold) between the embedding 150 and embeddings of the frames of the given result video 165. The computing system 135 can initialize the result video 165 in the graphical element 1010 of the graphical user interface 1000.

The result videos 165 can be sorted or organized in the element 1010 by the sorter 160. The result videos 165 can be sorted based on a distance or similarity measure, e.g., k-nearest neighbors distance. The distance or similarity measure can be a similarity between the embedding 150 of the medical query image 140 and the embedding of initial frames of the result videos 165 displayed in the element 1010. The element 1010 can display a video name or file name of each result video 165, the frame number of each result video 165 that the videos 165 are initiated at, and the similarity or distance measure (e.g., k-nearest neighbors distance).

Referring now to FIGS. 11A-F, among others, a graphical user interface 1100 where a selection of a medical query image 140 is used to search a collection of medical procedure videos is shown. The graphical user interface 1100 can receive a selection 1110 of a portion or subset of an image 1115. For example, via the graphical user interface 1100, a user can draw a box on the image 1115, crop the medical query image, highlight information in the medical query image, or otherwise select a group or set of pixels of image 1115. For example, a user can select pixels corresponding to an object, such as a medical instrument, a surgical arm, a surgical blade, biological matter, a polyp, an organ, or a lining of a cavity.

Responsive to receiving the selection 1110, the computing system 135 can set the medical query image 140 to be the selection 1110. The computing system 135 can generate the embedding 150 from the selection 1110. The searcher 155 can search the embedding 150 generated from the selection 1110 against the video collection 130 to retrieve the result videos 165. The retrieved result videos 165 can be displayed in the interface 1105. Furthermore, the computing system 135 can perform matching or object recognition based on the result videos 165 to identify the medical equipment or biological matter in the result videos 165 that matches the medical equipment or biological matter selected from the image 1115 via the selection 1110. The selection 1110 can be made to focus on a specific too, instrument, texture, or region within the image 1115. The computing system 135 can render a bounding box or other identifier within the result videos 165 to highlight the matching surgical equipment or biological matter. In view of the selection 1120, a user can focus on one object, such as a tool, and ignore other aspects of the image, such as a polyp. With the bounding box selection 1120, a user can indicate what particular areas of an image the search technique should focus on.

Figure 12:
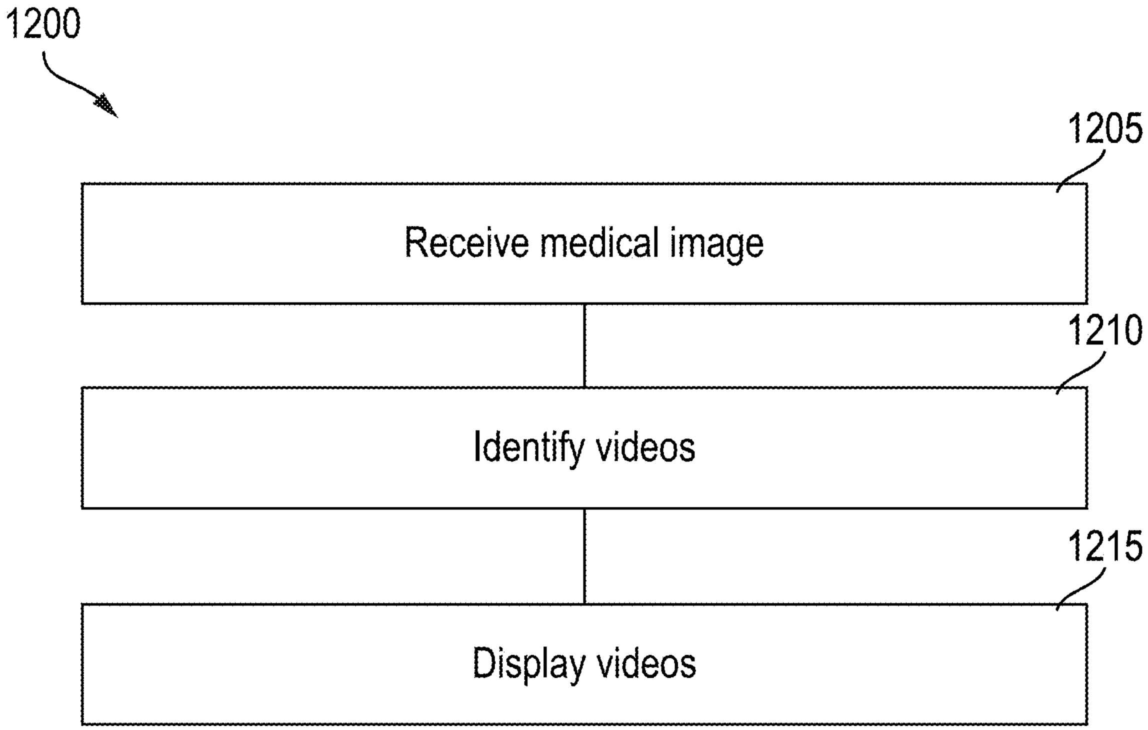
FIG. 12 depicts an example method of medical video searching.

Referring now to FIG. 12, among others, a method 1200 of medical video searching with self-supervised machine learning is shown. At least a portion of the method 1200 can be performed by the computing system 135. At least a portion of the method 1200 can be performed by the hub 105. The method 1200 can include an ACT 1205 of receiving a medical image. The method 1200 can include an ACT 1210 of identifying videos. The method 1200 can include an ACT 1215 of displaying videos.

At ACT 1205, the method 1200 can include receiving, by the computing system 135, a medical image. The medical image can be the medical query image 140. The computing system 135 can receive the medical query image 140 from a user device via the graphical user interface 1000. A medical practitioner can view or scan through a video of a medical procedure via the element 1005. The medical practitioner can select a particular frame of the user by interacting or pressing an element 1020 in the graphical user interface 1000. Responsive to receiving the selection via the element 1020, the computing system 135 can set the frame selected in the graphical user interface 1000 as the medical query image 140 to query the video collection 130 with.

At ACT 1210, the method 1200 can include identifying, by the computing system 135, videos. The computing system 135 can search the video collection 130 with the medical query image 140. The computing system 135 can generate a search query with the medical query image 140. The computing system 135 can generate the search query with a model established for a type of medical procedure. The medical query image 140 can be an image of a medical procedure, and the computing system 135 can generate the search query with the model established for the type of medical procedure.

The computing system 135 can select a feature extractor 145 from a set or group of feature extractors 145. Each feature extractor can be a model trained by machine learning, such as a self-supervised machine learning technique. The computing system 135 can receive a label or identifier identifying the type of medical procedure that the medical query image 140 is captured for. The data processing system 135 can select a feature extractor 145 established for the type of medical procedure. For example, the feature extractors 145 can include labels or identifiers identifying the type of the medical procedure that the feature extractors 145 are trained. Responsive to detecting a match between the label of the medical query image 140 and a label of a feature extractor 145, the computing system 135 can process the medical query image 140 with the selected feature extractor 145. The feature extractor 145 can generate an embedding 150 from the medical query image 140. The embedding 150 can have a variety of different dimensions, and can be a vector or a tensor that provides a representation of the medical query image 140.

At ACT 1215, the method 1200 can include displaying, by the computing system 135, videos. The searcher 155 can search the embedding 150 against the video collection 130 to identify the result videos 165. The searcher 155 can perform a machine learning technique to determine a level of similarity or dissimilarity between the embedding 150 and embeddings of the video collection 130. For example, each cluster of videos or video segments in the video collection 130 can have a keyframe or embedding for the keyframe that the embedding 150 is compared against. The searcher 155 can perform a technique such as k-nearest neighbors to determine a level of similarity between the medical query image 140 and the keyframe embedding. The searcher 155 can select the cluster with the highest similarity to the embedding 150 or with a similarity level greater than a threshold. The searcher 155 can provide the videos of the cluster to the sorter 160 to be sorted and displayed in the graphical user interface 1000.

Figure 13:
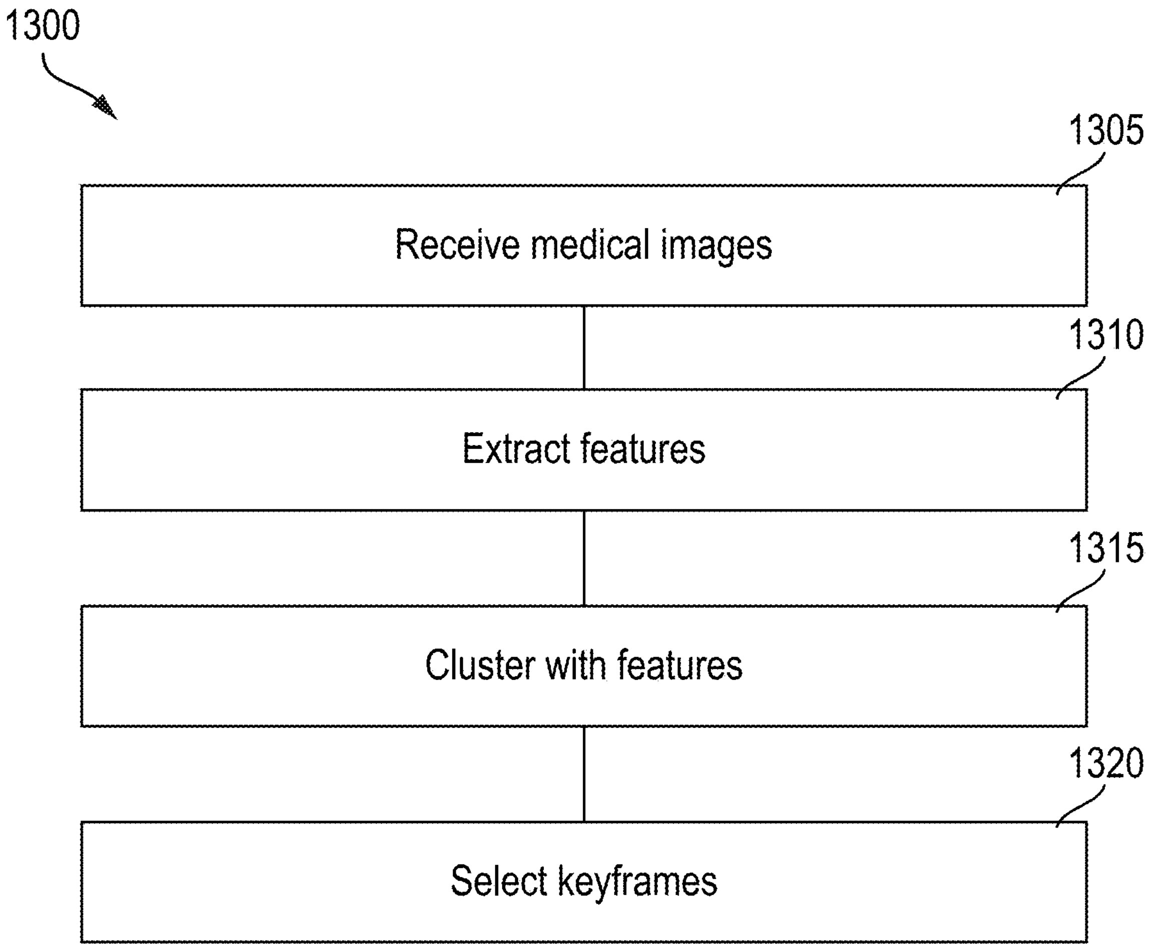
FIG. 13 depicts an example method of generating clusters of medical procedure videos for searching.

Referring now to FIG. 13, among others, an example method 1300 of generating clusters of medical procedure videos for searching is shown. At least a portion of the method 1300 can be performed by the computing system 135. At least a portion of the method 1300 can be performed by the hub 105. The method 1300 can include an ACT 1305 of receiving medical images. The method 1300 can include an ACT 1310 of extracting features. The method 1300 can include an ACT 1315 of clustering with features. The method 1300 can include an ACT 1320 of selecting keyframes.

At ACT 1305, the method 1300 can include receiving, by the hub 105, medical images. The medical videos can be images collected from various different medical procedures. For example, the video collector 110 can collect videos of various medical procedures and organize or sort the videos based on procedure type. For example, the video collector 110 can form a set or collection of videos for retroflection and another set or collection of videos for biopsy. The video collector 110 can form collections of videos for irrigation, retroflection, biopsy, or polypectomy. The hub 105 or computing system 120 can train a machine learning model for each group or class of videos. The result of the training can be a feature extractor 115 or the feature extractor 145 trained for each type of medical procedure.

At ACT 1310, the method 1300 can include extracting, by the computing system 120, features. The hub 105 can extract or generate features or embeddings from the collected videos via the feature extractor 115. The feature extractor 115 can extract features of the collected videos, segment the videos into parts, identify landmarks, identify temporal actions, or generate embeddings of the images or features of the videos.

At ACT 1315, the method 1300 can include clustering, by the computing system 120, features. For example, the clusterer 125 can generate clusters of videos, frames, or segments of the collected videos. The clusterer 125 can generate multiple clusters with the features extracted by the feature extractor 115 by grouping semantically similar segments of videos together. The clusterer 125 can generate the clusters with video summarizations, e.g., keyframes, storyboards, static summaries, video skims. Furthermore, the clusterer 125 can generate the clusters with temporal action segmentation, where an untrimmed procedural video is segmented temporally into multiple clips that represent different actions and semantically similar segments are grouped. Furthermore, the clusterer 125 can perform temporal action detection and group semantically similar temporal actions. The clusterer 125 can implement temporally-weighted hierarchical clustering for unsupervised action segmentation (TW-FINCH).

At ACT 1320, the method 1300 can include selecting, by the computing system 120, keyframes 915. The computing system 120 can select the keyframes 915 to provide a representative frame for each cluster. The computing system 120 can select one keyframe 915 for each cluster. The computing system 120 can select multiple keyframes 915 for each cluster. The computing system 120 can select a number of keyframes 915 proportional to a total number of frames, videos, or video duration for a given cluster. The computing system 120 can select the keyframes 915 by identifying, via a similarity or dissimilarity metric or distance, a frame in the videos of the cluster that is representative of the videos of the cluster. For example, the computing system 120 can select keyframes 915 that have minimal dissimilarity, minimum dissimilarity, or dissimilarity less than a level to all or a set of other frames in the cluster. For example, the computing system 120 can select keyframes 915 that have maximum similarity or similarity greater than a level to all or a set of other frames in the cluster. For example, the keyframe 915 can be a medoid selected for a cluster. The keyframes 915 can be used to perform searching. For example, the searcher 155 can search the embedding 150 of the medical query image 140 against the embeddings of the keyframes 915 to identify a matching cluster.

Figure 14:
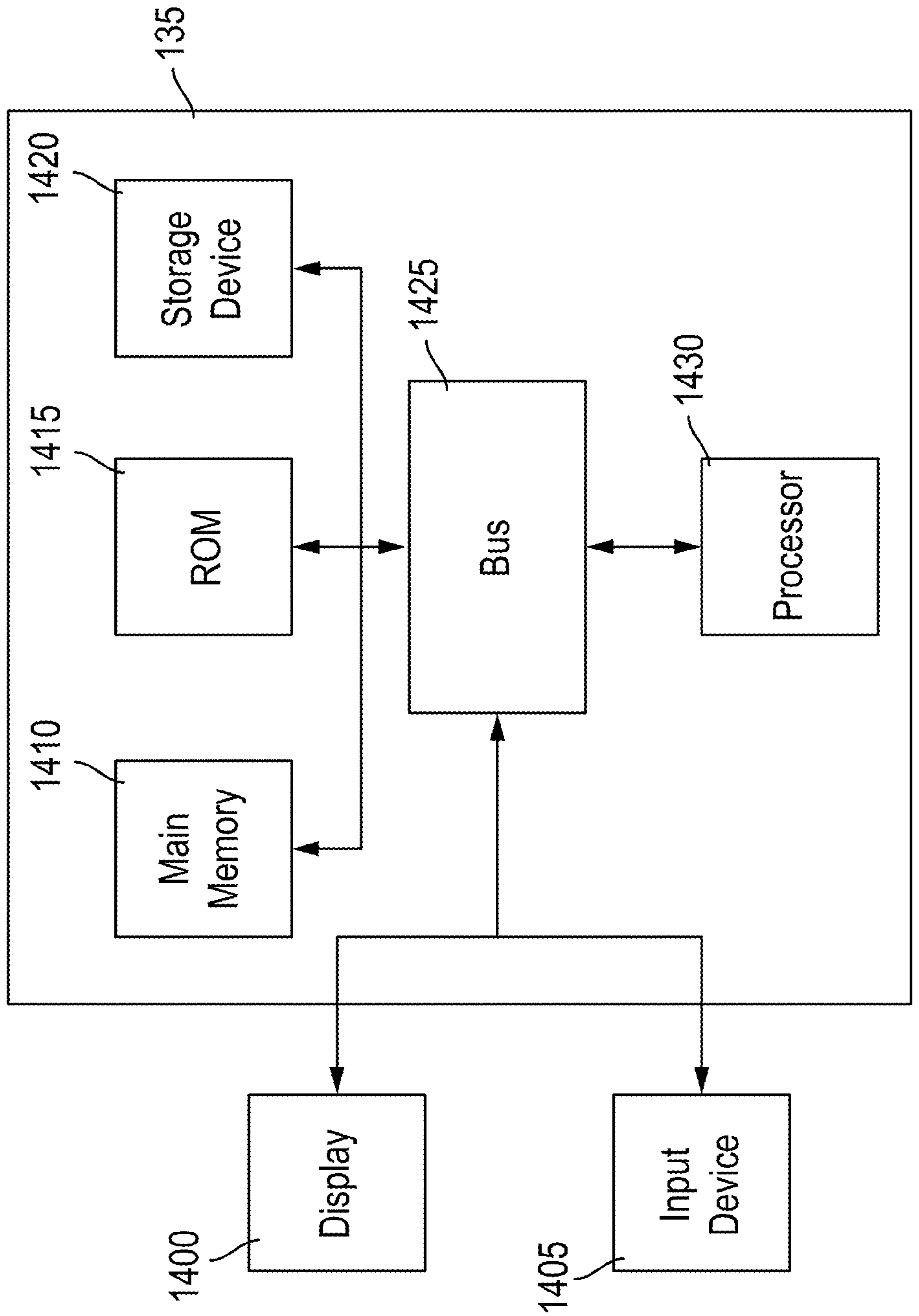
FIG. 14 depicts an example computing architecture of a data processing system.

Referring now to FIG. 14, among others, an example block diagram of a computing system 135 is shown. The computing system 135 can include or be used to implement a data processing system or its components. The architecture described in FIG. 14 can be used to implement the computing system 135, the hub 105, or the computing system 120. The computing system 135 can include at least one bus 1425 or other communication component for communicating information and at least one processor 1430 or processing circuit coupled to the bus 1425 for processing information. The computing system 135 can include one or more processors 1430 or processing circuits coupled to the bus 1425 for processing information. The computing system 135 can include at least one main memory 1410, such as a random access memory (RAM) or other dynamic storage device, coupled to the bus 1425 for storing information, and instructions to be executed by the processor 1430. The main memory 1410 can be used for storing information during execution of instructions by the processor 1430. The computing system 135 can further include at least one read only memory (ROM) 1415 or other static storage device coupled to the bus 1425 for storing static information and instructions for the processor 1430. A storage device 1420, such as a solid state device, magnetic disk or optical disk, can be coupled to the bus 1425 to persistently store information and instructions.

The computing system 135 can be coupled via the bus 1425 to a display 1400, such as a liquid crystal display, or active matrix display. The display 1400 can display information to a user. An input device 1405, such as a keyboard or voice interface can be coupled to the bus 1425 for communicating information and commands to the processor 1430. The input device 1405 can include a touch screen of the display 1400. The input device 1405 can include a cursor control, such as a mouse, a trackball, or cursor direction keys, for communicating direction information and command selections to the processor 1430 and for controlling cursor movement on the display 1400.

The processes, systems and methods described herein can be implemented by the computing system 135 in response to the processor 1430 executing an arrangement of instructions contained in main memory 1410. Such instructions can be read into main memory 1410 from another computer-readable medium, such as the storage device 1420. Execution of the arrangement of instructions contained in main memory 1410 causes the computing system 135 to perform the illustrative processes described herein. One or more processors in a multi-processing arrangement can be employed to execute the instructions contained in main memory 1410. Hard-wired circuitry can be used in place of or in combination with software instructions together with the systems and methods described herein. Systems and methods described herein are not limited to any specific combination of hardware circuitry and software.

Although an example computing system has been described in FIG. 14, the subject matter including the operations described in this specification can be implemented in other types of digital electronic circuitry, or in computer software, firmware, or hardware, including the structures disclosed in this specification and their structural equivalents, or in combinations of one or more of them.

Some of the description herein emphasizes the structural independence of the aspects of the system components or groupings of operations and responsibilities of these system components. Other groupings that execute similar overall operations are within the scope of the present application. Modules can be implemented in hardware or as computer instructions on a non-transient computer readable storage medium, and modules can be distributed across various hardware or computer based components.

The systems described above can provide multiple ones of any or each of those components and these components can be provided on either a standalone system or on multiple instantiations in a distributed system. In addition, the systems and methods described above can be provided as one or more computer-readable programs or executable instructions embodied on or in one or more articles of manufacture. The article of manufacture can be cloud storage, a hard disk, a CD-ROM, a flash memory card, a PROM, a RAM, a ROM, or a magnetic tape. In general, the computer-readable programs can be implemented in any programming language, such as LISP, PERL, C, C++, C#, PROLOG, Python, or in any byte code language such as JAVA. The software programs or executable instructions can be stored on or in one or more articles of manufacture as object code.

Example and non-limiting module implementation elements include sensors providing any value determined herein, sensors providing any value that is a precursor to a value determined herein, datalink or network hardware including communication chips, oscillating crystals, communication links, cables, twisted pair wiring, coaxial wiring, shielded wiring, transmitters, receivers, or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), or digital control elements.

The subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatuses. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. While a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices including cloud storage). The operations described in this specification can be implemented as operations performed by a data processing apparatus on data stored on one or more computer-readable storage devices or received from other sources.

The terms "computing device", "component" or "data processing apparatus" or the like encompass various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, app, script, or code) can be written in any form of programming language, including compiled or interpreted languages, declarative or procedural languages, and can be deployed in any form, including as a stand-alone program or as a module, component, subroutine, object, or other unit suitable for use in a computing environment. A computer program can correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit). Devices suitable for storing computer program instructions and data can include non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The subject matter described herein can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or a combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While operations are depicted in the drawings in a particular order, such operations are not required to be performed in the particular order shown or in sequential order, and all illustrated operations are not required to be performed. Actions described herein can be performed in a different order.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. ACTs, elements and features discussed in connection with one implementation are not intended to be excluded from a similar role in other implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any ACT or element being based on any information, act or element may include implementations where the act or element is based at least in part on any information, act, or element.

Any implementation disclosed herein may be combined with any other implementation or example, and references to "an implementation," "some implementations," "one implementation" or the like are not necessarily mutually exclusive and are intended to indicate that a particular feature, structure, or characteristic described in connection with the implementation may be included in at least one implementation or example. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

What is claimed is:

1. A system, comprising:

one or more processors, coupled with memory, to:

receive a search request comprising an image of a medical procedure and an indication of a type of the medical procedure;

select, based on the type of the medical procedure, a model trained to generate one or more search queries using images of the type of the medical procedure, the model selected from a plurality of models trained to generate search queries using images of medical procedures of different medical procedure types;

generate, responsive to the search request, a search query by executing the selected model with the image as an input;

identify, based at least on the search query, one or more videos of the type of the medical procedure from a collection of videos; and display, via a graphical user interface, the one or more videos of the type of the medical procedure.

2. The system of claim 1, wherein the one or more processors are further configured to:

train the model with a training dataset and a self-supervision machine learning process, the training dataset including a plurality of images without labels of medical information in the plurality of images.

3. The system of claim 1, wherein the one or more processors are further configured to:

receive, from a user device, a label of medical information included in the image of the medical procedure; and save the label to the collection of videos responsive to a selection of the collection of videos with the search query.

4. The system of claim 1, wherein the one or more processors are further configured to:

generate the graphical user interface to include a video of the medical procedure;

receive, via the graphical user interface, a selection of the image from the video of the medical procedure;

search, with an embedding, the collection of videos responsive to the selection of the image; and generate data to cause the graphical user interface to display frames of the collection of videos.

5. The system of claim 1, wherein the one or more processors are further configured to:

generate a plurality of embeddings of the collection of videos with a second model trained with self-supervised machine learning; and search, with an embedding, the plurality of embeddings of the collection of videos to select the collection of videos.

6. The system of claim 1, wherein the one or more processors are further configured to:

select, with the indication of the type of the medical procedure, the model from the plurality of models, at least two models of the plurality of models trained on images of the medical procedures of the different medical procedure types; and generate an embedding of the image with the selected model.

7. The system of claim 1, wherein the one or more processors are further configured to:

generate a plurality of embeddings of the collection of videos with a second model trained with self-supervised machine learning;

cluster the plurality of embeddings into a plurality of clusters; and search, with an embedding, the plurality of clusters to select a cluster of the plurality of clusters including embeddings of the collection of videos.

8. The system of claim 1, wherein the one or more processors are further configured to:

generate a plurality of embeddings of the collection of videos with a second model trained with machine learning;

cluster the plurality of embeddings into a plurality of clusters with machine learning;

select a plurality of key frames for the plurality of clusters with a medoid selection process, the plurality of key frames to provide medoids for the plurality of clusters; and search, with an embedding, embeddings of the plurality of key frames to select a cluster of the plurality of clusters.

9. The system of claim 1, wherein the one or more processors are further configured to:

sort the collection of videos based on a level of similarity between the image and the collection of videos; and generate data to cause the graphical user interface to display the sorted collection of videos.

10. The system of claim 1, wherein the one or more processors are further configured to:

receive, via the graphical user interface, a selection of a portion of the image, the portion of the image including a medical instrument or biological matter; and generate an embedding of the image with the selection of the portion of the image.

11. The system of claim 1, wherein the plurality of models are trained to generate search embeddings using the images of the medical procedures of the different medical procedure types, wherein the search query is an embedding, and the one or more processors are further configured to:

generate, responsive to the search request, the embedding by executing the selected model with the image as the input; and execute a machine learning search, to identify, based at least on the embedding, the one or more videos of the type of the medical procedure from the collection of videos, wherein the machine learning search is configured to execute on the embeddings generated by the plurality of models.

12. A method, comprising:

receiving, by a data processing system comprising one or more processors, coupled with memory, a search request comprising an image of a medical procedure and an indication of a type of the medical procedure;

selecting, by the data processing system, based on the type of the medical procedure, a model trained to generate one or more search queries using images of the type of the medical procedure, the model selected from a plurality of models trained to generate search queries using images of medical procedures of different medical procedure types;

generating, by the data processing system, responsive to the search request, a search query by executing the selected model with the image as an input;

identifying, by the data processing system, based at least on the search query, one or more videos of the type of the medical procedure from a collection of videos; and displaying, by the data processing system, via a graphical user interface, the one or more videos of the type of the medical procedure.

13. The method of claim 12, comprising:

training, by the data processing system, the model with a training dataset and a self- supervision machine learning process, the training dataset including a plurality of images without labels of medical information in the plurality of images.

14. The method of claim 12, comprising:

receiving, by the data processing system, from a user device, a label of medical information included in the image of the medical procedure; and saving, by the data processing system, the label to the collection of videos responsive to a selection of the collection of videos with the search query.

15. The method of claim 12, comprising:

selecting, by the data processing system, with the indication of the type of the medical procedure, the model from the plurality of models, at least two models of the plurality of models trained on images of different medical procedures; and generating, by the data processing system, an embedding of the image with the selected model.

16. The method of claim 12, comprising:

generating, by the data processing system, a plurality of embeddings of the collection of videos with a second model trained with machine learning;

clustering, by the data processing system, the plurality of embeddings into a plurality of clusters with machine learning;

selecting, by the data processing system, a plurality of key frames for the plurality of clusters with a medoid selection process, the plurality of key frames to provide medoids for the plurality of clusters; and searching, by the data processing system, with an embedding, embeddings of the plurality of key frames to select a cluster of the plurality of clusters.

17. The method of claim 12, comprising:

receiving, by the data processing system, via the graphical user interface, a selection of a portion of the image, the portion of the image including a medical instrument or biological matter; and generating, by the data processing system, an embedding of the image with the selection of the portion of the image.

18. A non-transitory computer-readable medium storing processor-executable instructions that, when executed by one or more processors, cause the one or more processors to:

receive a search request comprising an image of a medical procedure and an indication of a type of the medical procedure;

select, based on the type of the medical procedure, a model trained to generate one or more search queries using images of the type of the medical procedure, the model selected from a plurality of models trained to generate search queries using images of medical procedures of different medical procedure types;

generate, responsive to the search request, a search query by executing the selected model with the image as an input;

identify, based at least on the search query, one or more videos of the type of the medical procedure from a collection of videos; and display, via a graphical user interface, the one or more videos of the type of the medical procedure.

19. The non-transitory computer-readable medium of claim 18, wherein the instructions cause the one or more processors to:

receive from a user device, a label of medical information included in the image of the medical procedure; and save the label to the collection of videos responsive to a selection of the collection of videos with the search query.

20. The non-transitory computer-readable medium of claim 18, wherein the instructions cause the one or more processors to:

receive via the graphical user interface, a selection of a portion of the image, the portion of the image including a medical instrument or biological matter; and generate an embedding of the image with the selection of the portion of the image.

* * * * *